United States Patent
Shibuya et al.

(10) Patent No.: US 10,249,823 B2
(45) Date of Patent: Apr. 2, 2019

(54) FULLERENE DERIVATIVES AND PHOTOELECTRIC DEVICES AND IMAGE SENSORS

(71) Applicant: Samsung Electronics Co., Ltd., Suwon-si, Gyeonggi-do (KR)

(72) Inventors: Hiromasa Shibuya, Suwon-si (KR); Tadao Yagi, Hwaseong-si (KR); Rie Sakurai, Suwon-si (KR); Yeong Suk Choi, Suwon-si (KR); Yutaka Matsuo, Tokyo (JP)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/822,400

(22) Filed: Nov. 27, 2017

(65) Prior Publication Data

US 2019/0019955 A1 Jan. 17, 2019

(30) Foreign Application Priority Data

Jul. 12, 2017 (KR) .................. 10-2017-0088287

(51) Int. Cl.
*C07C 23/46* (2006.01)
*H01L 51/00* (2006.01)
(Continued)

(52) U.S. Cl.
CPC .......... *H01L 51/0047* (2013.01); *C07C 23/46* (2013.01); *C07C 25/18* (2013.01);
(Continued)

(58) Field of Classification Search
CPC ............... H01L 51/0047; H01L 27/307; H01L 51/0046; H01L 51/424; H01L 51/001; C07C 2604/00
See application file for complete search history.

(56) References Cited

U.S. PATENT DOCUMENTS 7,371,479 B2 * 5/2008 Nuber .................. C07C 35/44
423/445 B
8,304,643 B2 11/2012 Nakamura et al.
(Continued)

FOREIGN PATENT DOCUMENTS

JP 3313405 B2 8/2002
JP 2007217350 A 8/2007
(Continued)

OTHER PUBLICATIONS

Chang-Zhi Li, et al., "Regioselective synthesis of tetra(aryl)-mono(silylmethyl)[60]fullerenes and derivatization to methanofullerene compound", Tetrahedron 67 (2011) pp. 9944-9949.
(Continued)

*Primary Examiner* — Jasmine Clark
(74) *Attorney, Agent, or Firm* — Harness, Dickey & Pierce, P.L.C.

(57) ABSTRACT

A fullerene derivative may be included in photoelectric devices and image sensor. Optical absorption characteristics of a thin film including the fullerene derivative may be shifted toward a short wavelength compared with those of the thin film including the unsubstituted C60 fullerene, for example, a thin film including the fullerene derivative may be associated with a peak absorption wavelength ($\lambda_{max}$) that is be shorter than that of a thin film including the unsubstituted C60 fullerene.

19 Claims, 8 Drawing Sheets

(51) Int. Cl.
*C07C 25/18* (2006.01)
*H01L 51/42* (2006.01)
*H01L 27/30* (2006.01)

(52) U.S. Cl.
CPC ........ *C07C 2604/00* (2017.05); *H01L 27/307* (2013.01); *H01L 51/001* (2013.01); *H01L 51/424* (2013.01)

(56) References Cited

U.S. PATENT DOCUMENTS 9,039,935 B2 5/2015 Nakamura et al.
9,231,214 B2 1/2016 Tolbert et al.
2015/0060775 A1 3/2015 Liang et al.

FOREIGN PATENT DOCUMENTS

JP 2011026339 A 2/2011
WO WO-2007129768 A1 11/2007

OTHER PUBLICATIONS

Yutaka Matsuo et al., "Organic and Organometallic Derivatives of Dihydrogen-Encapsulated[60]Fullerene", J. Am. Chem. Soc. 2005, 127, pp. 17148-17149.

Jung-Hao Chang et al., "Efficient Inverted Quasi-Bilayer Organic Solar Cells Fabricated by Using Non-Halogenated Solvent Processes" J. Mater. Chem. A, 2014, 2, 13398-13406.

Sebastian Doring et al., "Highly sensitive wide range organic photodiode based on zinc phthalocyanine:C60", Phys. Status Solidi A 213, No. 9, 2387-2391 (2016) / DOI 10.1002/pssa.201532856.

Masaya Sawamura et al., "Single-step synthesis of pentaaryl-monohydro[60]fullerenes through fivefold addition of organocopper reagent to C60", Journal of Organometallic Chemistry 599 (2000) 32-36.

Takaaki, Niinomi et al., "Penta(organo)[60]fullerenes as acceptors for organic photovoltaic cells", J. Mater. Chem., 2009, 19, 5804-5811.

Yutaka Matsuo et al., "Synthesis of 6,9,12,15,18-Pentamethyl-1,6,9,12,15,18-Hexahydro(C60-lh)[5,6]Fullerene", Organic Syntheses, vol. 83, p. 80-87 (2006); Coll. vol. 11, p. 319-326 (2009).

Masaya Sawamura et al., "Hybrid of Ferrocene and Fullerene", J. Am. Chem. Soc. 2002, 124, 9354-9355.

Toshihiko Kaji, et al., "Molecular Orientation and Electronic Structure of Epitaxial Bucky Ferrocene (Fe(C60(CH3)5)C5H5) Thin Films", *J. Phys. Chem. B* 2004, 108, 9914-9918.

Eiichi Nakamura, "Bucky ferrocene. Hybrid of ferrocene and fullerene", *Pure Appl. Chem.*, vol. 75, No. 4, pp. 427-434, 2003.

Dirk M. Guldi et al., "Sharing Orbitals: Ultrafast Excited State Deactivations with Different Outcomes in Bucky Ferrocenes and Ruthenocenes", J. Am. Chem. Soc. 2006, 128, 9420-9427.

* cited by examiner

FULLERENE DERIVATIVES AND PHOTOELECTRIC DEVICES AND IMAGE SENSORS

CROSS-REFERENCE TO RELATED APPLICATIONS

This application claims priority to and the benefit of, under 35 U.S.C. § 119, Korean Patent Application No. 10-2017-0088287 filed in the Korean Intellectual Property Office on Jul. 12, 2017, the entire contents of which are incorporated herein by reference.

BACKGROUND

1. Field

Fullerene derivatives, photoelectric devices, and image sensors are disclosed.

2. Description of the Related Art

Fullerene is a molecule having a closed-cage structure comprising carbon atoms. Fullerene may be used in various fields due to its stable structure and satisfactory electric characteristics. Recently, various fullerene derivatives have been developed by combining the fullerene molecule with a substituent.

Photoelectric devices may convert light (e.g., incident light) into electrical signals based on using photoelectric effects. A given photoelectric device may include a photodiode, a phototransistor, and the like, and it may be included in an electronic device, such as an image sensor.

SUMMARY

Some example embodiments provide a novel compound including a novel fullerene derivative that may be applied to ("included in") a photoelectric device.

Some example embodiments provide a photoelectric device including the novel fullerene derivative.

Some example embodiments provide an image sensor including the photoelectric device.

According to some example embodiments, a compound including a fullerene derivative represented by Chemical Formula 1 is provided.

[Chemical Formula 1]

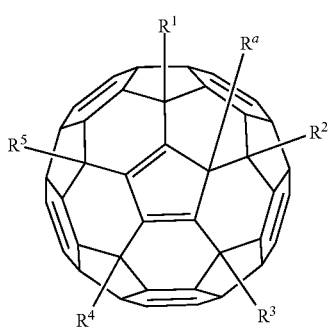

In Chemical Formula 1,
$R^a$ is hydrogen or a C1 to C10 alkyl group,
$R^1$ to $R^5$ are independently one of a substituted or unsubstituted C1 to C10 alkyl group, or a substituted or unsubstituted C6 to C12 aryl group, and
at least one of $R^1$ to $R^5$ is a C1 to C10 alkyl group substituted with at least one of a fluorine and a cyano group, or a C6 to C12 aryl group substituted with at least one of a fluorine and a cyano group.

The fullerene derivative may be a compound that is configured to be vacuum-deposited based on sublimation.

The fullerene derivative may have an about 10 wt % weight loss relative to an initial weight at a temperature of less than or equal to about 450° C., an about 50 wt % weight loss relative to an initial weight at a temperature of less than or equal to about 510° C., and an about 90 wt % weight loss relative to an initial weight at a temperature of less than or equal to about 600° C., when the fullerene derivative is performed a thermogravimetric analysis at 1 Pa or less.

The fullerene derivative may have a LUMO energy level of about 3.7 eV to about 5.0 eV and a HOMO energy level of about 5.8 eV to about 7.0 eV.

$R^1$ to $R^5$ of Chemical Formula 1 may independently be one of a C1 to C10 alkyl group substituted with at least one of a fluorine and a cyano group, or a C6 to C12 aryl group substituted with at least one of a fluorine and a cyano group.

The fullerene derivative may be represented by one of Chemical Formulae 1a to 1l.

[Chemical Formula 1a]

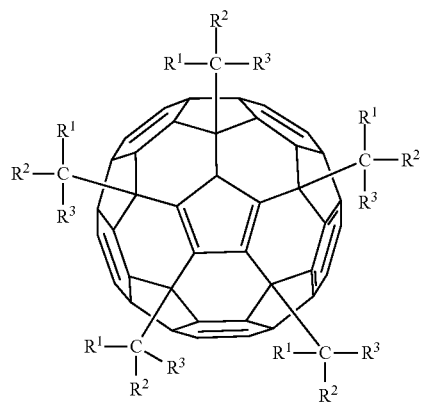

[Chemical Formula 1b]

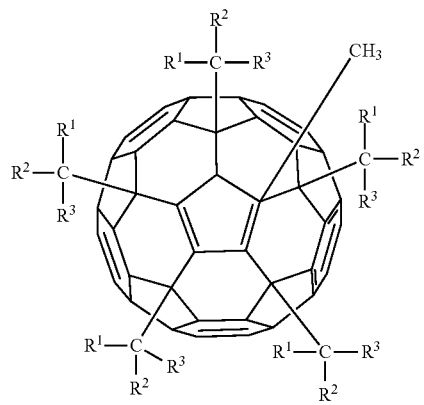

[Chemical Formula 1c]
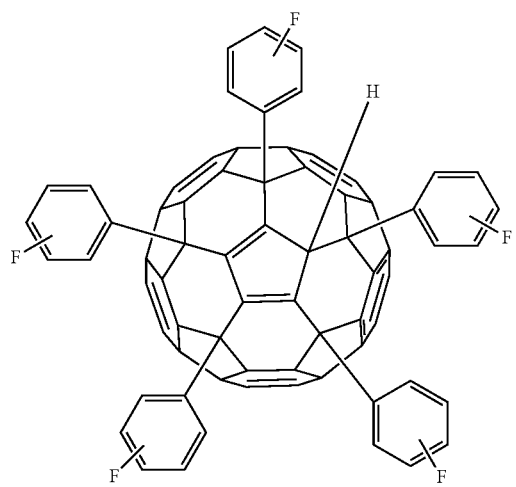
[Chemical Formula 1d]
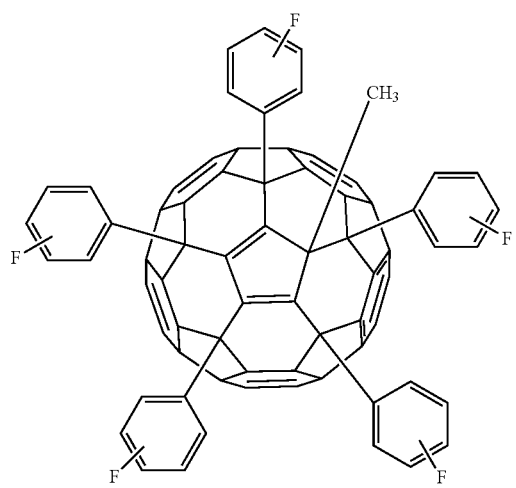
[Chemical Formula 1e]
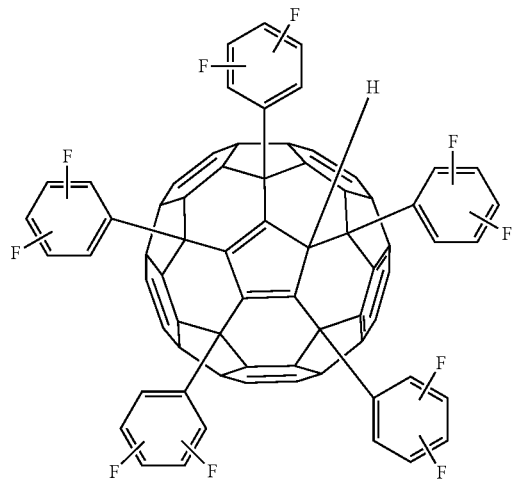
[Chemical Formula 1f]
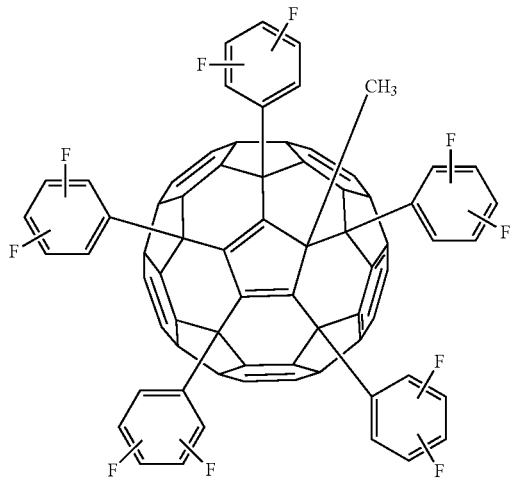
[Chemical Formula 1g]
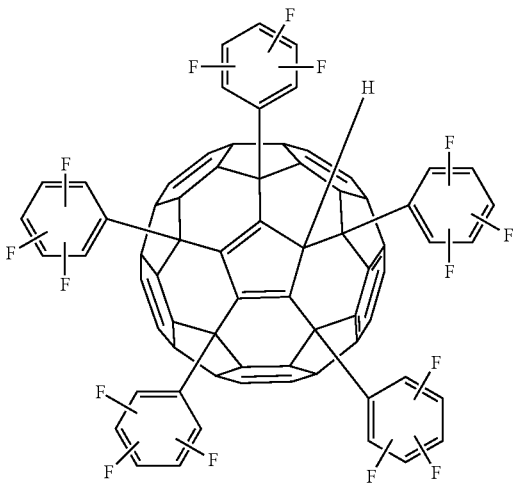
[Chemical Formula 1h]
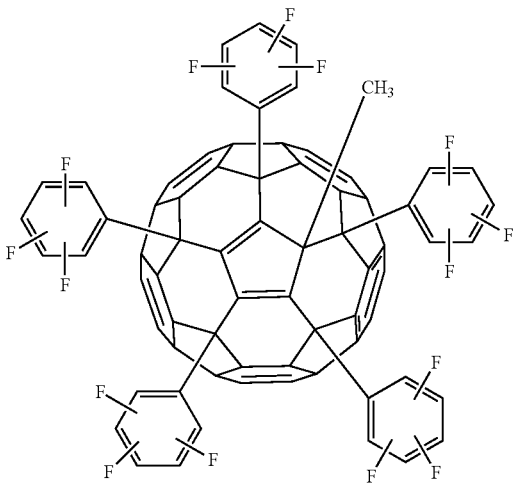

[Chemical Formula 1i]

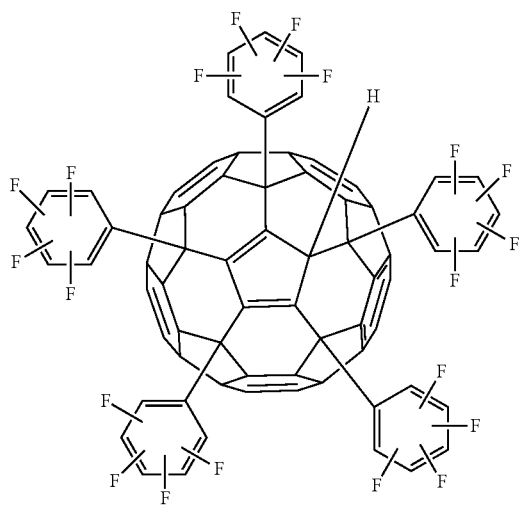

[Chemical Formula 1j]

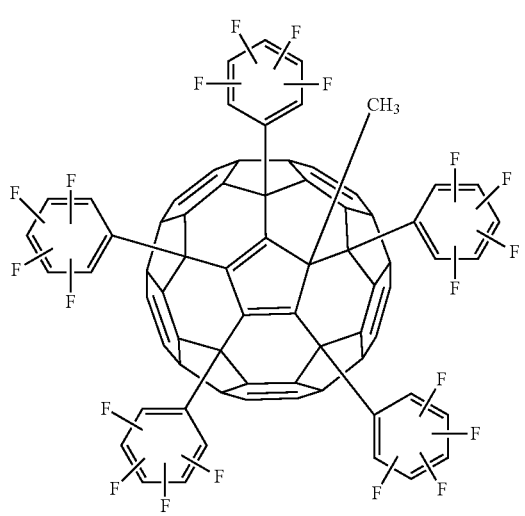

[Chemical Formula 1k]

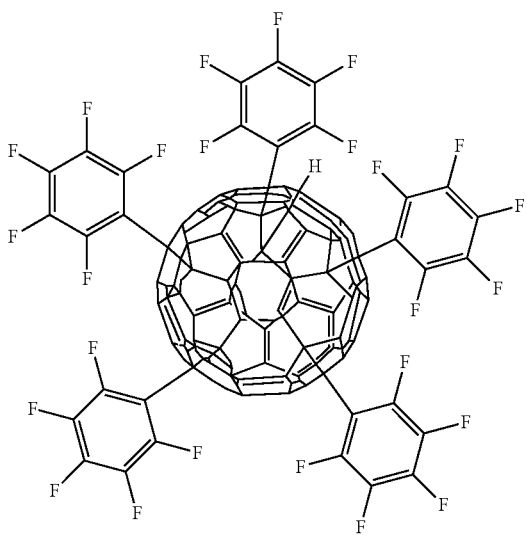

[Chemical Formula 1l]

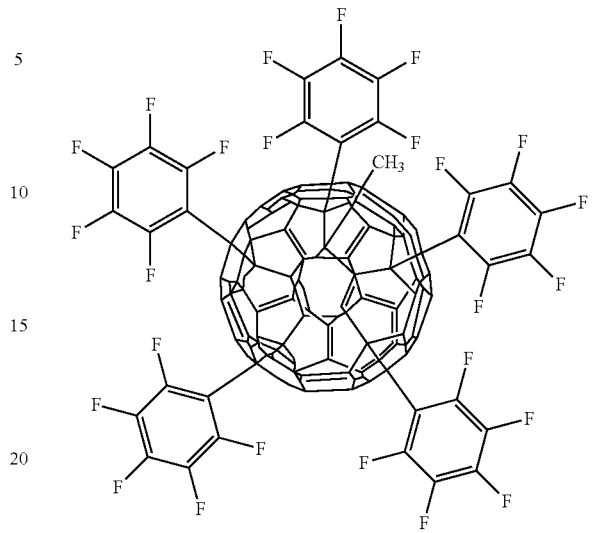

In Chemical Formulae 1a and 1b, $R^1$ to $R^3$ are independently one of hydrogen or fluorine and at least one of $R^1$ to $R^3$ is fluorine.

According to some example embodiments, a thin film including the compound is provided.

A peak absorption wavelength ($\lambda_{max}$) of the thin film may be shorter than a peak absorption wavelength ($\lambda_{max}$) of a thin film including C60 fullerene.

According to yet some example embodiments, a photoelectric device includes a first electrode and a second electrode facing each other and an organic layer disposed between the first electrode and the second electrode, wherein the organic layer includes fullerene derivative represented by Chemical Formula 1.

[Chemical Formula 1]

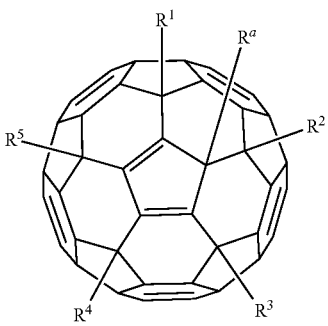

In Chemical Formula 1,
$R^a$ is hydrogen or a C1 to C10 alkyl group,
$R^1$ to $R^5$ are independently one of a substituted or unsubstituted C1 to C10 alkyl group or a substituted or unsubstituted C6 to C12 aryl group, and
at least one of $R^1$ to $R^5$ is a C1 to C10 alkyl group substituted with at least one of a fluorine and a cyano group, or a C6 to C12 aryl group substituted with at least one of a fluorine and a cyano group.

$R^1$ to $R^5$ of Chemical Formula 1 may independently be one of a C1 to C10 alkyl group substituted with at least one of fluorine and a cyano group, or a C6 to C12 aryl group substituted with at least one of fluorine and a cyano group.

The fullerene derivative may be represented by one of Chemical Formulae 1a to 1l.
[Chemical Formula 1a]
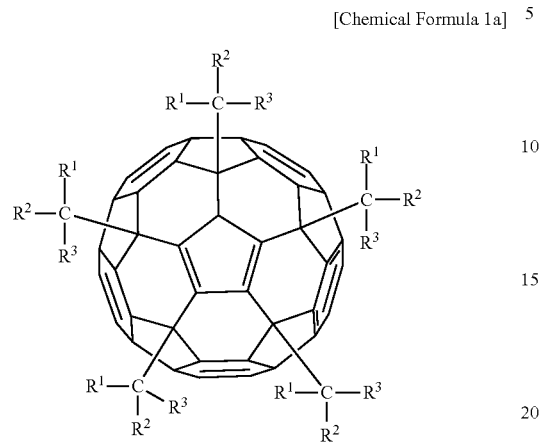
[Chemical Formula 1b]
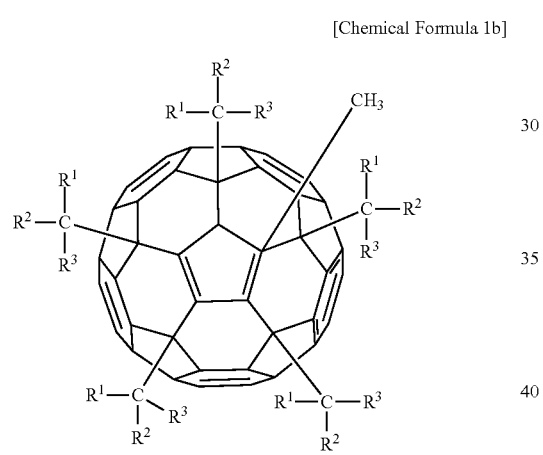
[Chemical Formula 1c]
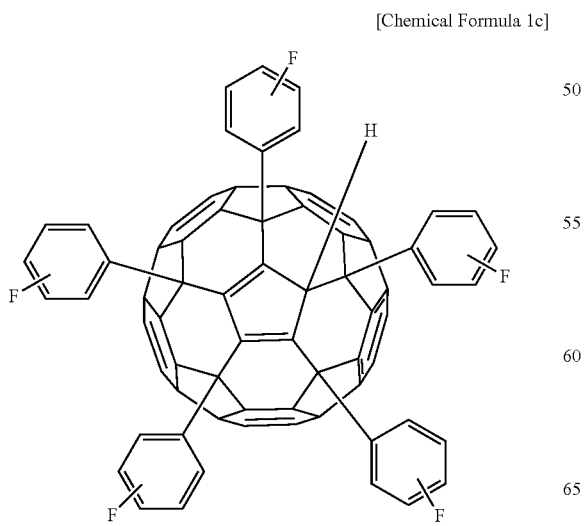
[Chemical Formula 1d]
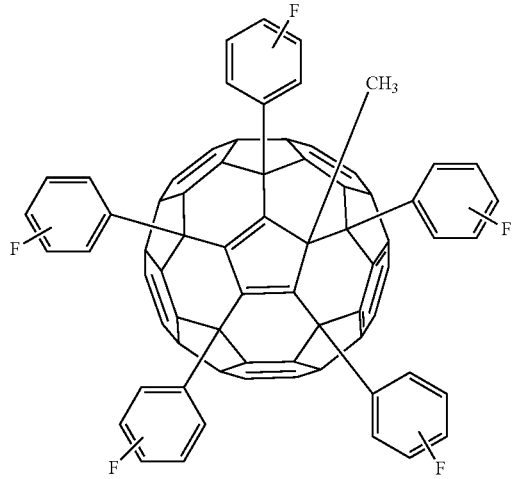
[Chemical Formula 1e]
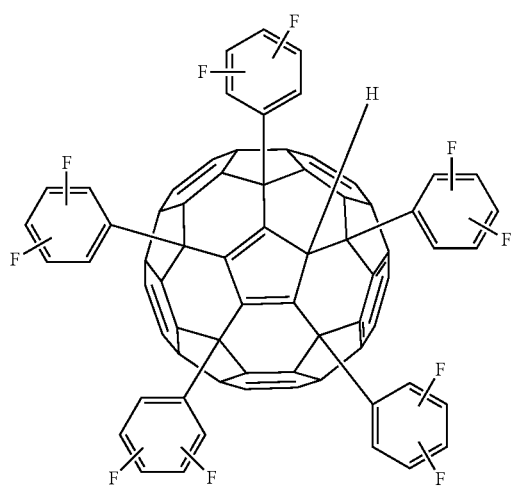
[Chemical Formula 1f]
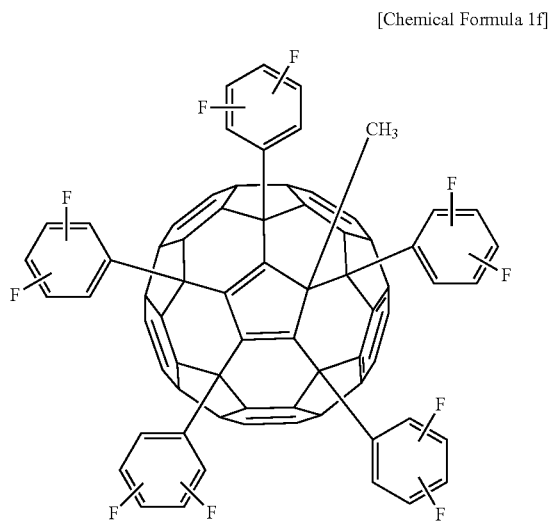

[Chemical Formula 1g]
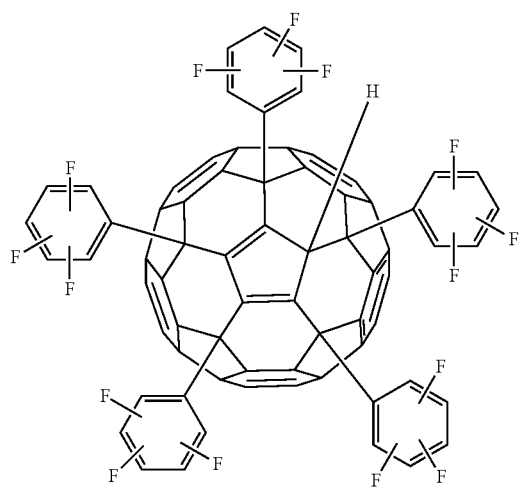
[Chemical Formula 1h]
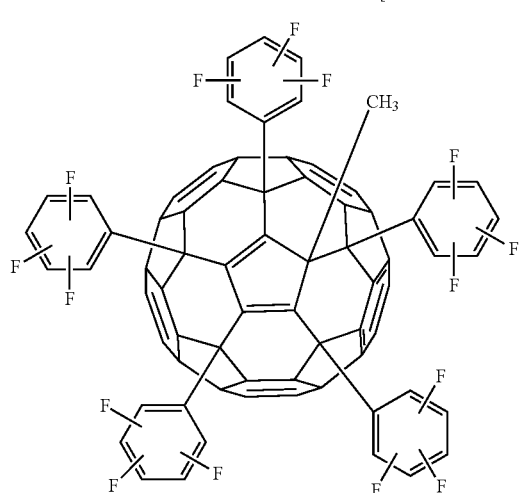
[Chemical Formula 1i]
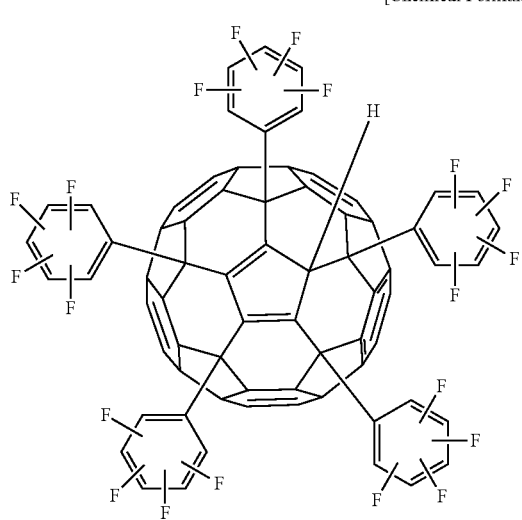
[Chemical Formula 1j]
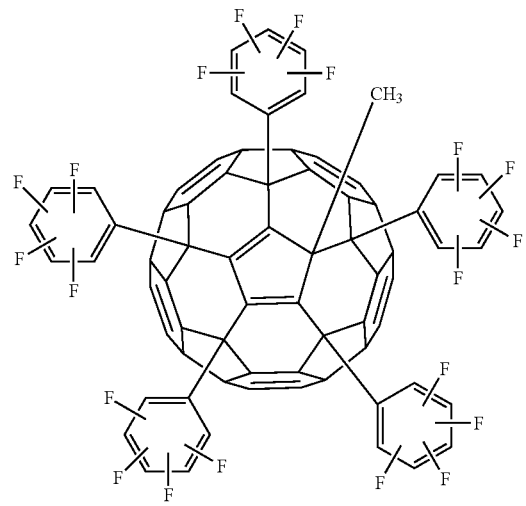
[Chemical Formula 1k]
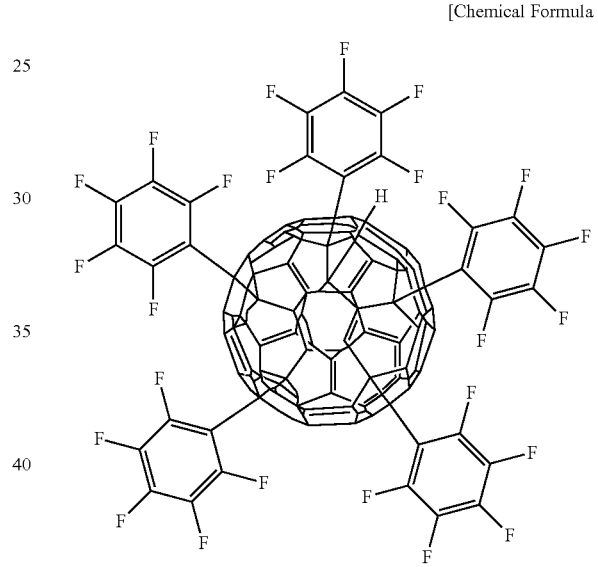
[Chemical Formula 1l]
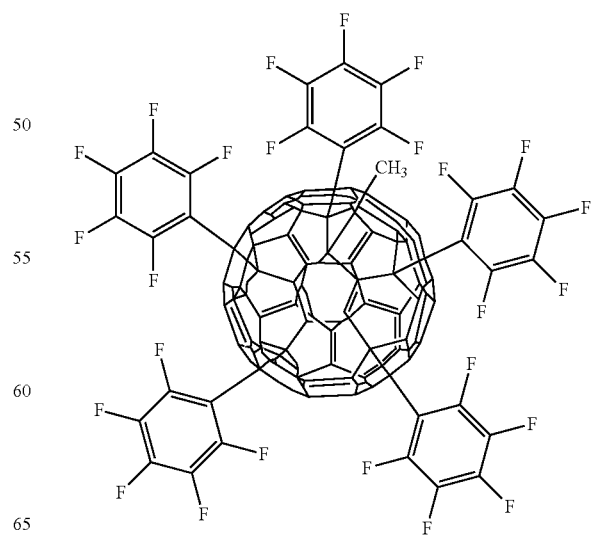

In Chemical Formulae 1a and 1b, $R^1$ to $R^3$ is hydrogen or fluorine and at least one of $R^1$ to $R^3$ is a fluorine.

The organic layer may include an active layer, the active layer may include a p-type semiconductor and an n-type semiconductor that at least partially comprise a pn junction, and the n-type semiconductor may include the fullerene derivative.

The p-type semiconductor and the n-type semiconductor may be configured to be co-deposited based on sublimation.

The fullerene derivative may have a LUMO energy level of about 3.7 eV to about 5.0 eV and a HOMO energy level of about 5.8 eV to about 7.0 eV.

The p-type semiconductor may have a LUMO energy level of about 3.0 eV to about 3.6 eV and a HOMO energy level of about 5.1 eV to about 5.7 eV.

The p-type semiconductor may be a light absorbing material having a core structure including an electron donating moiety, a π conjugation linking group, and an electron-accepting moiety.

The p-type semiconductor may include a compound represented by Chemical Formula 2.

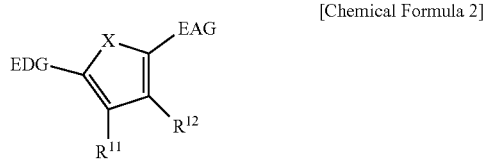

[Chemical Formula 2]

In Chemical Formula 2,
X is Se, Te, SO, $SO_2$, or $SiR^aR^b$,
EDG is an electron donating group,
EAG is an electron accepting group,
$R^{11}$, $R^{12}$, $R^a$, and $R^b$ are independently one of hydrogen or a monovalent substituent.

According to some example embodiments, an electronic device includes the photoelectric device.

According to yet some example embodiments, an image sensor includes the photoelectric device.

The fullerene derivative satisfying optical characteristics and electric characteristics is provided and characteristics of a photoelectric device and an electronic device including the same may be improved.

DETAILED DESCRIPTION

Figure 1:
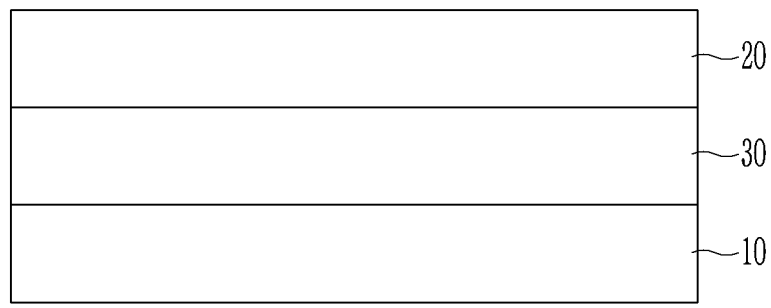
FIG. 1 is a cross-sectional view showing a photoelectric device according to some example embodiments.

Hereinafter, example embodiments of the present disclosure will be described in detail so that a person skilled in the art would understand the same. This disclosure may, however, be embodied in many different forms and is not construed as limited to the example embodiments set forth herein.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

Hereinafter, 'a combination' refers to a mixture of two or more and a stack structure of two or more.

As used herein, when a definition is not otherwise provided, 'substituted' refers to replacement of hydrogen of a compound by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

Hereinafter, a fullerene derivative according to some example embodiments is described.

A fullerene derivative according to some example embodiments is represented by Chemical Formula 1.

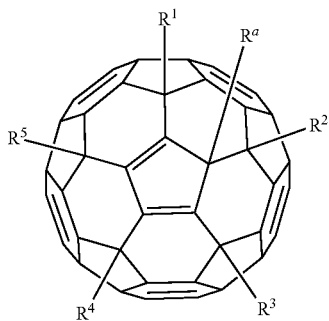

[Chemical Formula 1]

In Chemical Formula 1, $R^a$ is hydrogen or a C1 to C10 alkyl group, $R^1$ to $R^5$ are independently one of a substituted or unsubstituted C1 to C10 alkyl group or a substituted or unsubstituted C6 to C12 aryl group, and at least one of $R^1$ to $R^5$ is a C1 to C10 alkyl group substituted with a fluorine, a cyano group, or a combination thereof or a C6 to C12 aryl group substituted with a fluorine, a cyano group, or a combination thereof.

The fullerene derivative has a 5-substituted or 6-substituted structure at a particular position and thus may increase a steric hindrance but decrease a pi conjugation structure (a π-conjugation system) compared with an unsubstituted C60 fullerene. Accordingly, the fullerene derivative may reduce an aggregation during the deposition and thus improve deposition characteristics and suppress transformation of optical properties such as a shift of an absorption wavelength spectrum of light, which may be caused by the aggregation, compared with the unsubstituted C60 fullerene.

The fullerene derivative may be configured to be vacuum-deposited, for example, vacuum-deposited through ("based on") sublimation. The vacuum deposition through sublimation may be confirmed by performing a thermogravimetric analysis (TGA), for example, the fullerene derivative may have an about 10 wt % weight loss relative to an initial weight at less than or equal to about 450° C., an about 50 wt % weight loss relative to an initial weight at less than or equal to about 510° C., and an about 90 wt % weight loss relative to an initial weight at less than or equal to about 600° C.

For example, the fullerene derivative may be configured to have, at a pressure of 1 Pa or less, an about 10 wt % weight loss relative to an initial weight at about 300° C. to about 400° C., an about 50 wt % weight loss relative to an initial weight at about 380° C. to about 450° C., and a greater than or equal to about 90 wt % weight loss relative to an initial weight at about 430° C. to about 500° C., for example in the thermogravimetric analysis. Within the range, the about 10 wt % weight loss relative to the initial weight may for example occur at about 310° C. to about 380° C., the about 50 wt % weight loss relative to the initial weight may occur at about 400° C. to about 430° C., and greater than or equal to about 90 wt % weight loss may occur relative to the initial weight at about 460° C. to about 490° C.

The fullerene derivative may have ("may be associated with") a LUMO energy level of about 3.7 eV to about 5.0 eV and a HOMO energy level of about 5.8 eV to about 7.0 eV, a LUMO energy level of about 3.8 eV to about 4.9 eV and a HOMO energy level of about 6.0 eV to about 6.9 eV, a LUMO energy level of about 3.8 eV to about 4.8 eV and a HOMO energy level of about 6.0 eV to 6.7 eV, or a LUMO energy level of about 3.8 eV to about 4.5 eV and a HOMO energy level of about 6.0 eV to about 6.5 eV. The fullerene derivative may have for example an energy band gap of about 2.0 eV to about 2.3 eV. When the fullerene derivative has an energy level within the ranges, it may be configured to be used as an n-type semiconductor effectively.

For example, $R^1$ to $R^5$ of Chemical Formula 1 may independently be a C1 to C10 alkyl group substituted with fluorine, a cyano group, or a combination thereof ("at least one of a fluorine and a cyano group") or a C6 to C12 aryl group substituted with a fluorine, a cyano group, or a combination thereof.

For example, $R^1$ to $R^5$ of Chemical Formula 1 may independently be an alkyl group substituted with one fluorine, a phenyl group substituted with one fluorine, a biphenyl group substituted with one fluorine, or a naphthyl group substituted with one fluorine.

For example, $R^1$ to $R^5$ of Chemical Formula 1 may independently be an alkyl group substituted with two fluorines, a phenyl group substituted with two fluorines, a biphenyl group substituted with two fluorines, or a naphthyl group substituted with two fluorines.

For example, $R^1$ to $R^5$ of Chemical Formula 1 may independently be an alkyl group substituted with three fluorines, a phenyl group substituted with three fluorines, a biphenyl group substituted with three fluorines, or a naphthyl group substituted with three fluorines.

For example, $R^1$ to $R^5$ of Chemical Formula 1 may independently be an alkyl group substituted with four fluorines, a phenyl group substituted with four fluorines, a biphenyl group substituted with four fluorines, or a naphthyl group substituted with four fluorines.

For example, $R^1$ to $R^5$ of Chemical Formula 1 may independently be an alkyl group substituted with five fluorines, a phenyl group substituted with five fluorines, a biphenyl group substituted with five fluorines, or a naphthyl group substituted with five fluorines.

For example, $R^1$ to $R^5$ of Chemical Formula 1 may independently be an alkyl group substituted with one cyano group, a phenyl group substituted with one cyano group, a biphenyl group substituted with one cyano group, or a naphthyl group substituted with one cyano group.

For example, $R^1$ to $R^5$ of Chemical Formula 1 may independently be an alkyl group substituted with two cyano groups, a phenyl group substituted with two cyano groups, a biphenyl group substituted with two cyano groups, or a naphthyl group substituted with two cyano groups.

For example, $R^1$ to $R^5$ of Chemical Formula 1 may independently be an alkyl group substituted with three cyano groups, a phenyl group substituted with three cyano groups, a biphenyl group substituted with three cyano groups, or a naphthyl group substituted with three cyano groups.

For example, $R^1$ to $R^5$ of Chemical Formula 1 may independently be an alkyl group substituted with four cyano groups, a phenyl group substituted with four cyano groups, a biphenyl group substituted with four cyano groups, or a naphthyl group substituted with four cyano groups.

For example, $R^1$ to $R^5$ of Chemical Formula 1 may independently be an alkyl group substituted with five cyano groups, a phenyl group substituted with five cyano groups, a biphenyl group substituted with five cyano groups, or a naphthyl group substituted with five cyano groups.

The fullerene derivative may be for example represented by one of Chemical Formulae 1a to 1l, but is not limited thereto.

[Chemical Formula 1a]

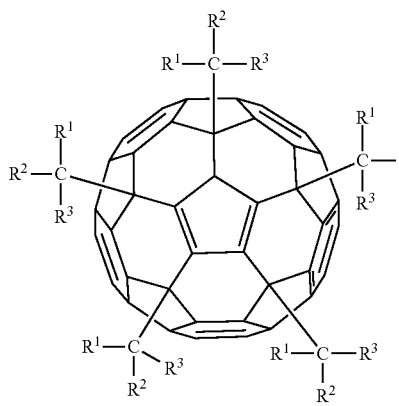

[Chemical Formula 1b]

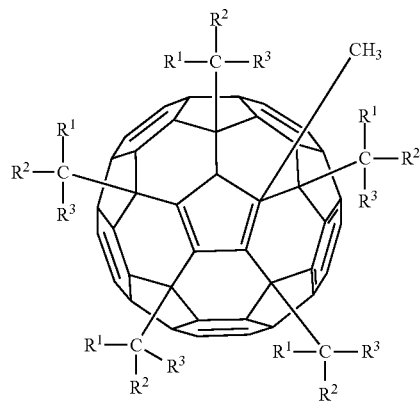

[Chemical Formula 1c]

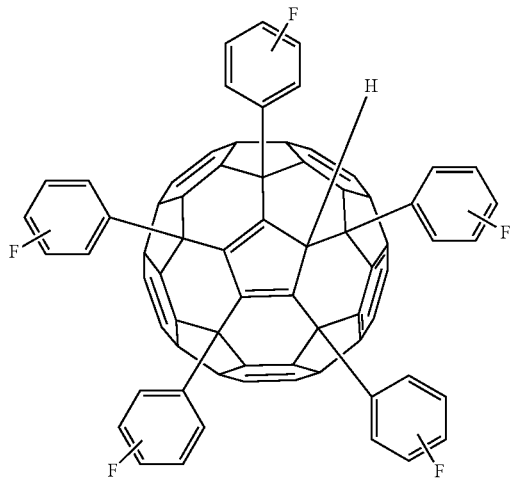

[Chemical Formula 1d]

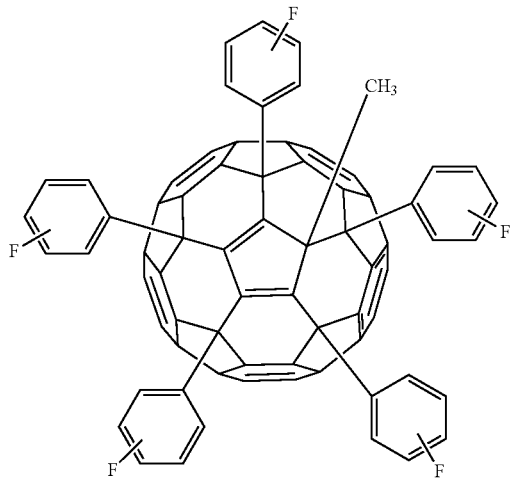

[Chemical Formula 1e]
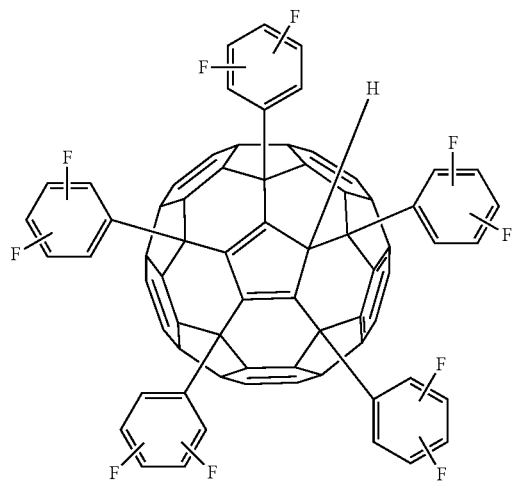
[Chemical Formula 1f]
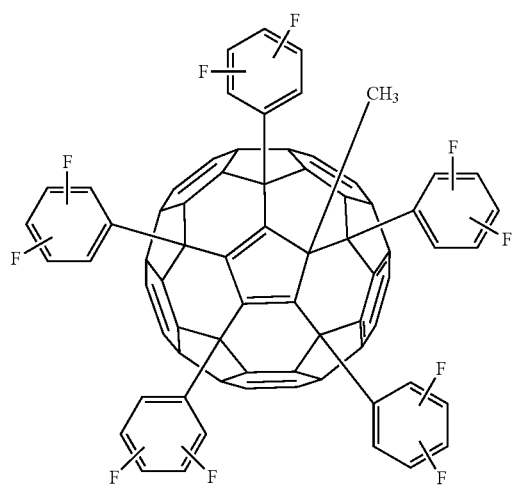
[Chemical Formula 1g]
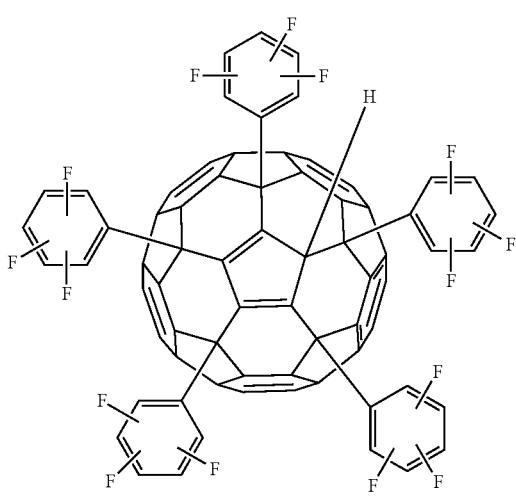
[Chemical Formula 1h]
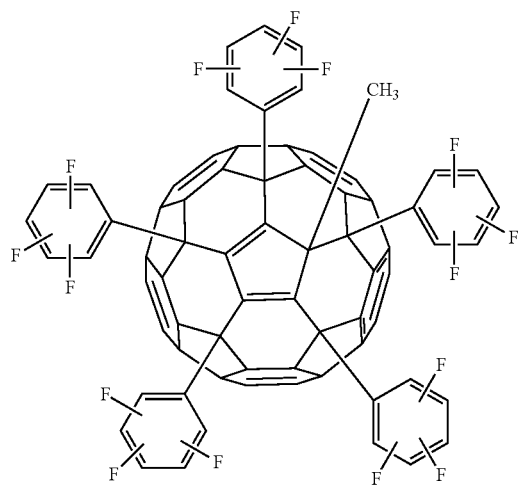
[Chemical Formula 1i]
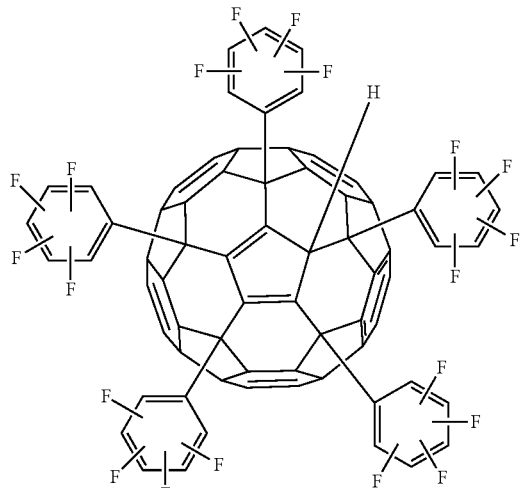
[Chemical Formula 1j]
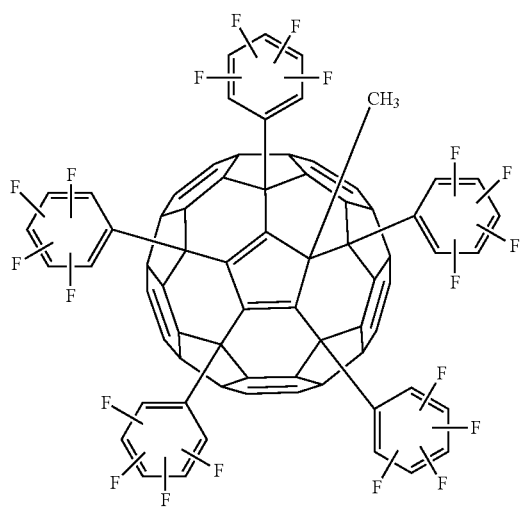

-continued

[Chemical Formula 1k]

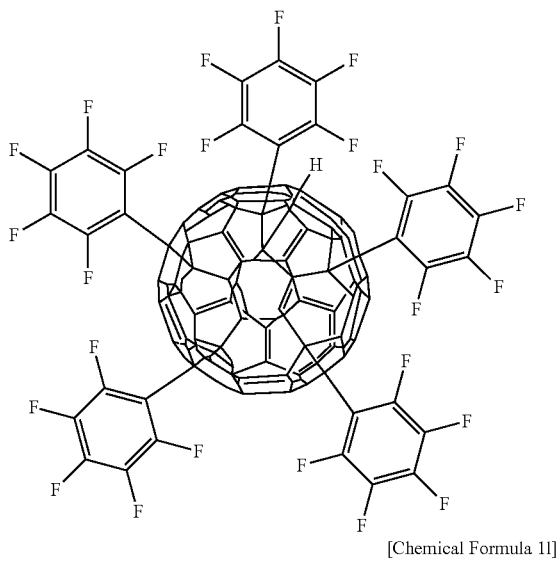

[Chemical Formula 1l]

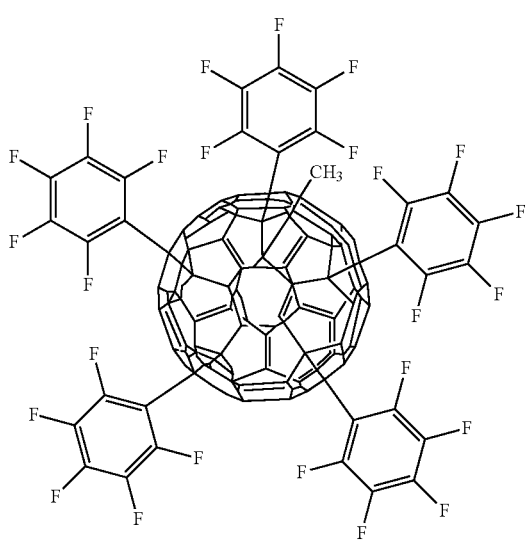

In Chemical Formulae 1a and 1b, $R^1$ to $R^3$ are independently one of hydrogen or fluorine and at least one of $R^1$ to $R^3$ is fluorine.

The fullerene derivative may be configured to be vacuum-deposited through ("based on") sublimation into a thin film as described above. The thin film may maintain ("may be configured to maintain") inherent characteristics of the fullerene derivative without breaking and/or transforming a chemical bond of the fullerene derivative, and accordingly, transformation of optical properties of the thin film may be reduced, compared with transformation of the optical properties due to an aggregation during deposition of a thin film including an unsubstituted C60 fullerene. For example, optical absorption characteristics of the thin film including the fullerene derivative may be shifted toward a short wavelength compared with those of the thin film including the unsubstituted C60 fullerene, for example, a thin film including the fullerene derivative may be associated with a peak absorption wavelength ($\lambda_{max}$) that is be shorter than that of the thin film including the unsubstituted C60 fullerene.

Hereinafter, a photoelectric device including the fullerene derivative is described.

FIG. 1 is a cross-sectional view showing a photoelectric device according to some example embodiments.

Referring to FIG. 1, a photoelectric device 100 according to some example embodiments includes a first electrode 10 and a second electrode 20 facing each other and an organic layer 30 disposed between ("interposing between") the first electrode 10 and the second electrode 20.

A substrate (not shown) may be disposed on a surface of the first electrode 10 or a surface of the second electrode 20. The substrate may be for example made of (may at least partially comprise) an inorganic material such as glass, an organic material such as polycarbonate, polymethylmethacrylate, polyethyleneterephthalate, polyethylenenaphthalate, polyamide, polyethersulfone, or a combination thereof, or a silicon wafer. The substrate may be omitted.

One electrode of the first electrode 10 and the second electrode 20 may be an anode and the other may be a cathode. For example, the first electrode 10 may be an anode and the second electrode 20 may be a cathode.

At least one electrode of the first electrode 10 and the second electrode 20 may be a light-transmitting electrode and the light-transmitting electrode may be for example made of ("may at least partially comprise") a conductive oxide such as an indium tin oxide (ITO), indium zinc oxide (IZO), zinc oxide (ZnO), tin oxide (SnO), aluminum tin oxide (AITO), and fluorine doped tin oxide (FTO), or a metal thin layer of a single layer or a multilayer. When one electrode of the first electrode 10 and the second electrode 20 is a non-light-transmitting electrode, it may be made of ("may at least partially comprise") for example an opaque conductor such as aluminum (Al), silver (Ag), or gold (Au). For example, the first electrode 10 and the second electrode 20 may be all light-transmitting electrodes. For example, the second electrode 20 may be a light receiving electrode disposed at a light receiving side (e.g., on a side of the photoelectric device 100 that is configured to receive incident light from an external environment).

The organic layer 30 may include an active layer.

The active layer may be a layer including a p-type semiconductor and an n-type semiconductor to at least partially comprise a pn junction, which is a layer configured to produce excitons based on receiving light from outside (e.g., incident light from the external environment) and then separating holes and electrons from the produced excitons. The n-type semiconductor may include the fullerene derivative.

The p-type semiconductor and the n-type semiconductor may be light absorbing materials that are configured to absorb at least one part of each visible wavelength spectrum of light and for example the p-type semiconductor may be a light absorbing material that may absorb light in a wavelength spectrum of light of greater than or equal to about 400 nm and less than 500 nm ("a blue wavelength spectrum of light"), about 500 nm to about 600 nm ("a green wavelength spectrum of light"), and/or greater than about 600 nm and less than or equal to about 700 nm ("a red wavelength spectrum of light") and the n-type semiconductor may be a fullerene derivative.

For example, the p-type semiconductor may be a light absorbing material that may selectively absorb light in a wavelength spectrum of light of greater than or equal to about 400 nm and less than 500 nm, about 500 nm to about 600 nm, and greater about 600 nm and less than or equal to about 700 nm and the n-type semiconductor may be a fullerene derivative. For example, the p-type semiconductor may be a light absorbing material that may selectively absorb light ("may be configured to selectively absorb light") in a wavelength spectrum of light of about 500 nm to about 600 nm and the n-type semiconductor may be a fullerene derivative.

For example, the p-type semiconductor may be for example a light absorbing material having a LUMO energy level of about 3.0 eV to about 3.6 eV and a HOMO energy level of about 5.1 eV to about 5.7 eV. Within the ranges, the p-type semiconductor may be for example a light absorbing material having a LUMO energy level of about 3.1 eV to about 3.5 eV and a HOMO energy level of about 5.2 eV to about 5.6 eV.

For example, the p-type semiconductor may be for example a light absorbing material having a core structure including an electron donating moiety, a pi conjugation linking group, and an electron accepting moiety.

The p-type semiconductor is a compound having the core structure and may include for example a compound represented by Chemical Formula 2, but is not limited thereto.

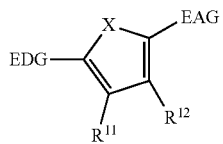

[Chemical Formula 2]

In Chemical Formula 2,
X is Se, Te, SO, SO$_2$, or SiR$^a$R$^b$,
EDG is an electron donating group,
EAG is an electron accepting group, and
R$^{11}$, R$^{12}$, R$^a$, and R$^b$ are independently ("independently one of") hydrogen or a monovalent substituent.

Herein, the monovalent substituent may be for example a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group, but is not limited thereto.

The p-type semiconductor may be for example a light absorbing material represented by Chemical Formula 2A, but is not limited thereto.

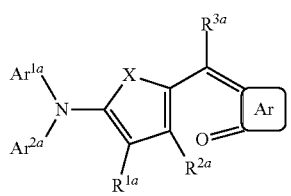

[Chemical Formula 2A]

In Chemical Formula 2A,
X is Se, Te, SO, SO$_2$, or SiR$^a$R$^b$,
Ar is a substituted or unsubstituted 5-membered ring, a substituted or unsubstituted 6-membered ring, or a condensed ring of two or more of the foregoing rings,
Ar$^{1a}$ and Ar$^{2a}$ are independently a substituted or unsubstituted C6 to C30 aryl group or a substituted or unsubstituted C3 to C30 heteroaryl group, Ar$^{1a}$ and Ar$^{2a}$ are independently present or linked with each other by a linker of G$^1$ to form ("at least partially comprise") a ring, wherein G$^1$ is one of a single bond, —(CR$^g$R$^h$)$_{n2}$—, —O—, —S—, —Se—, —N=, —NR$^i$—, —SiR$^j$R$^k$—, and —GeR$^l$R$^m$— and n2 is 1 or 2, and R$^{1a}$ to R$^{3a}$, R$^a$, R$^b$, and R$^g$ to R$^m$ are independently hydrogen, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, halogen or cyano group.

The p-type semiconductor may be for example a light absorbing material represented by one chemical formula of Chemical Formulae 2A-1 to 2A-4 but is not limited thereto.

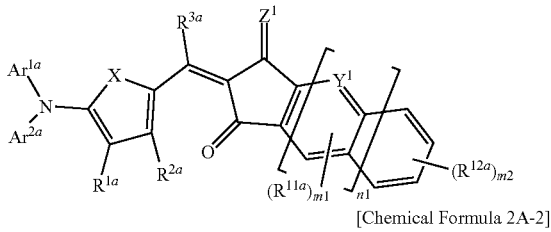

[Chemical Formula 2A-1]

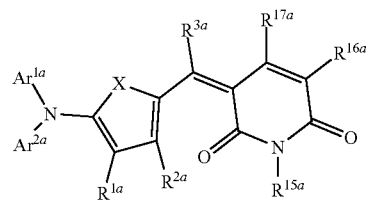

[Chemical Formula 2A-2]

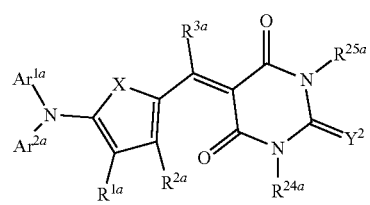

[Chemical Formula 2A-3]

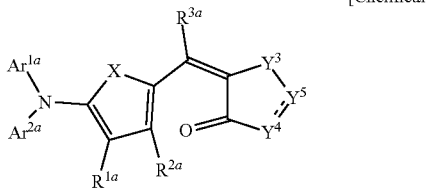

[Chemical Formula 2A-4]

In each chemical formula of Chemical Formulae 2A-1 to 2A-4,
X is Se, Te, SO, SO$_2$, or SiR$^a$R$^b$,
Z$^1$ is O or CR$^c$R$^d$,
Y$^1$ is N or CR$^e$,
Y$^2$ is one of O, S, Se, Te, and C(R$^f$)(CN),
Y$^3$ is O, S, Se, or Te,
Y$^4$ is N or NR$^{18a}$,
Y$^5$ is CR$^{19a}$ or C=CR$^{20a}$(CN),
Ar$^{1a}$ and Ar$^{2a}$ are independently a substituted or unsubstituted C6 to C30 aryl group or a substituted or unsubstituted C3 to C30 heteroaryl group, Ar$^{1a}$ and Ar$^{2a}$ are independently present or linked with each other to form ("at least partially comprise") a ring,
R$^{1a}$ to R$^{3a}$, R$^{11a}$, R$^{12a}$, R$^{15a}$ to R$^{20a}$, R$^{24a}$, R$^{25a}$, and R$^a$ to R$^f$ are independently ("independently one of") hydrogen, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, halogen or cyano group, n1 is 0 or 1, m1 is 0 or 1, and m2 is an integer ranging from 0 to 4.

The light absorbing material represented by one of Chemical Formulae 2A-1 to 2A-4 may be for example one compound of a plurality of compounds of Group 1 to Group 4, but is not limited thereto.

[Group 1]

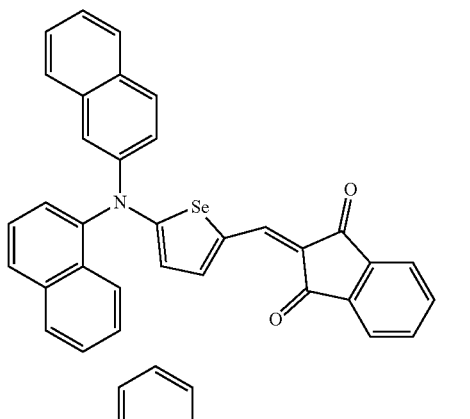

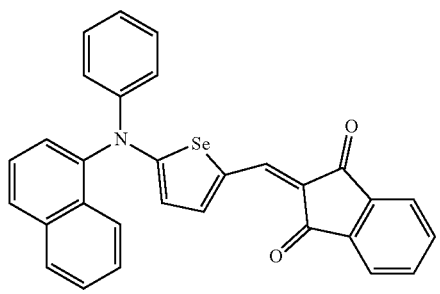

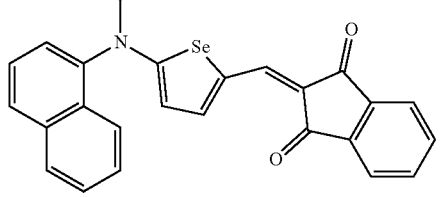

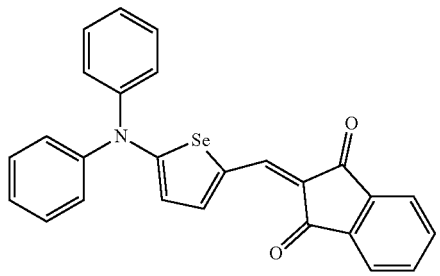

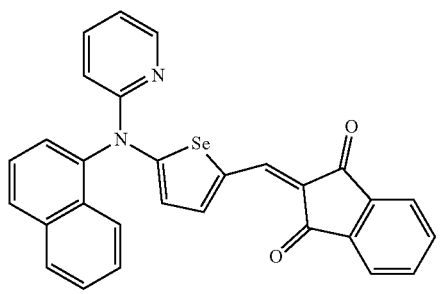

-continued

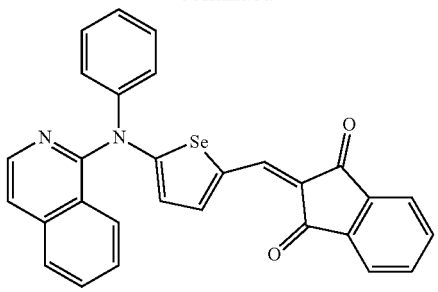

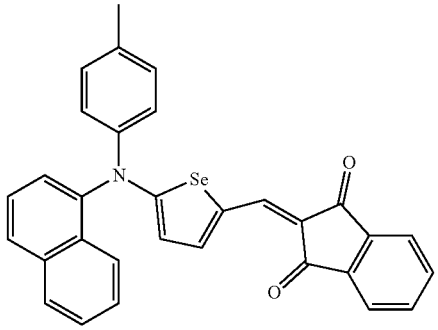

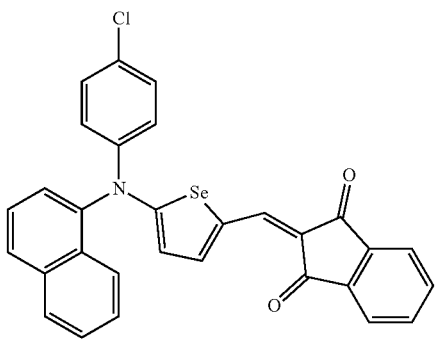

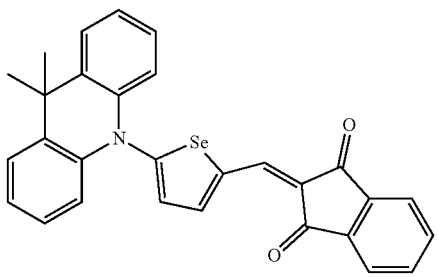

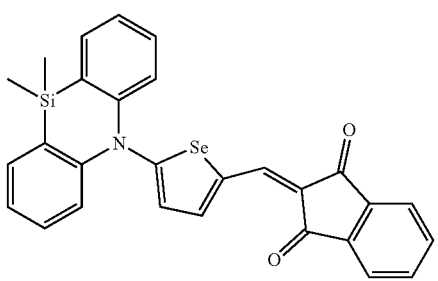

25
-continued
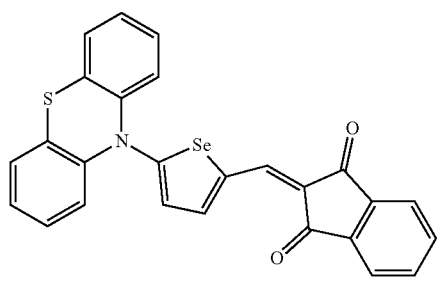
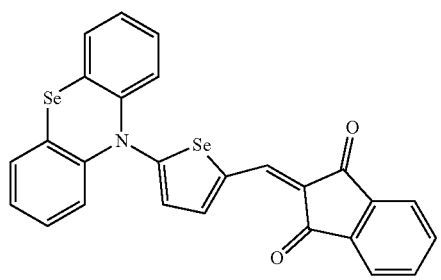
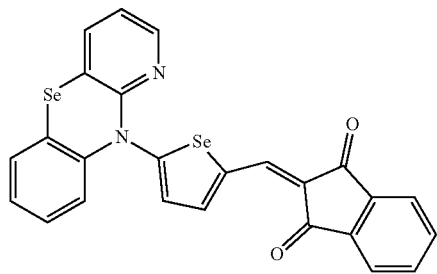
[Group 2]
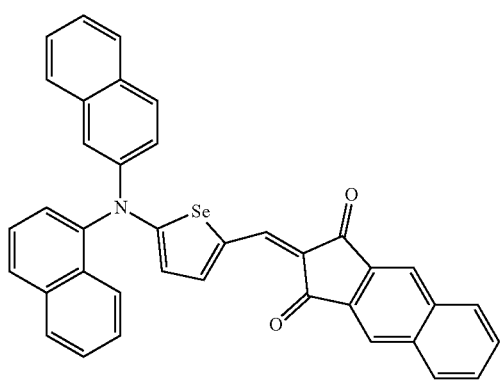
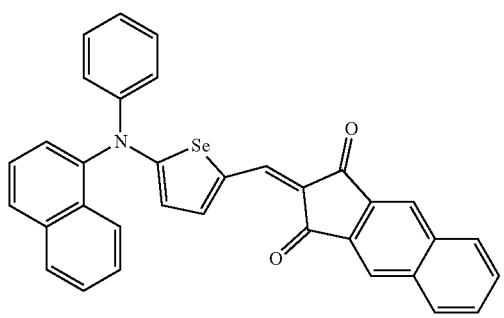
26
-continued
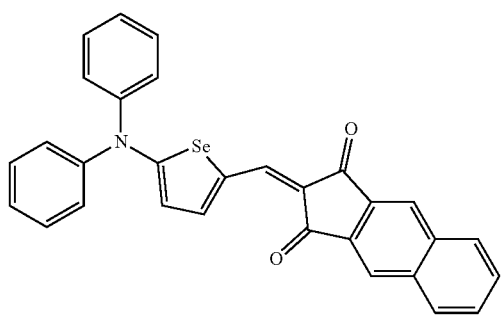
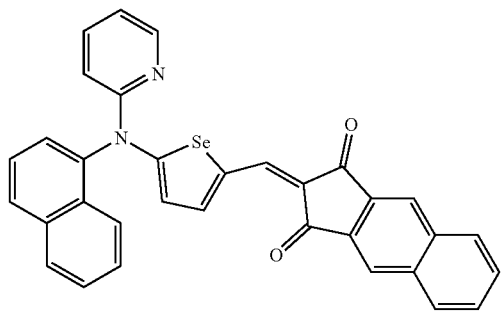
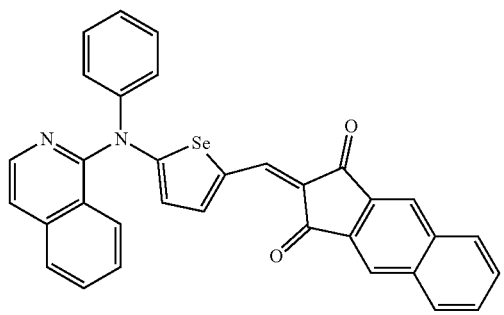
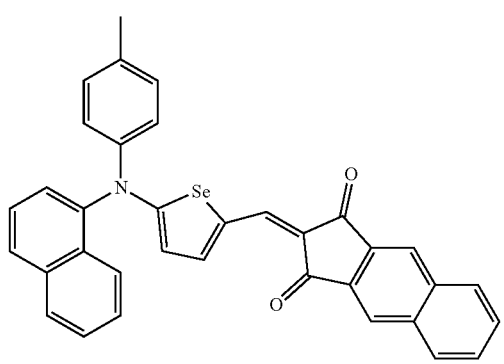
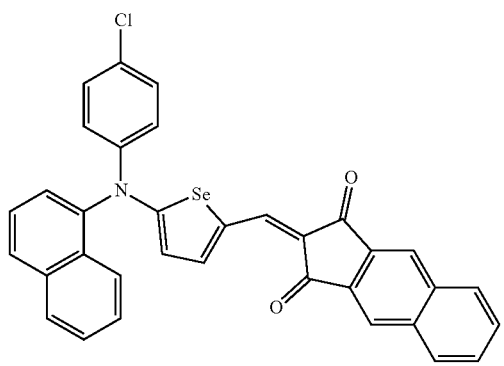

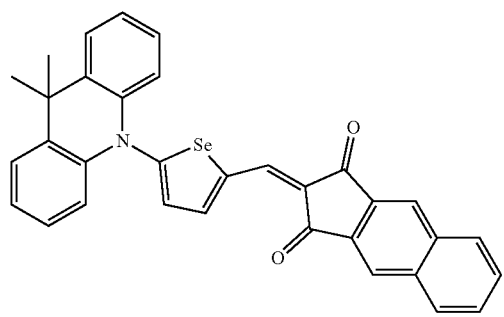
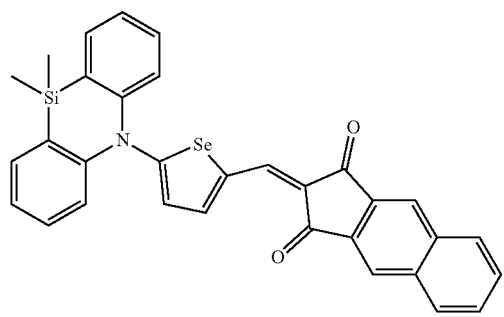
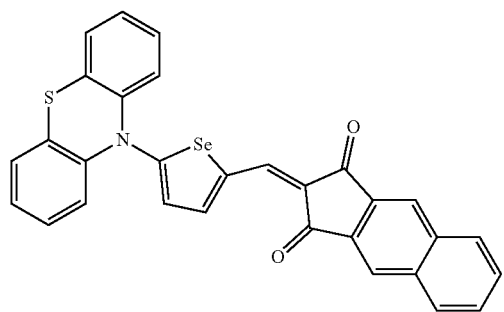
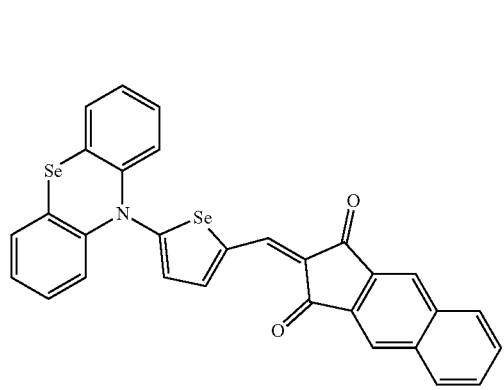
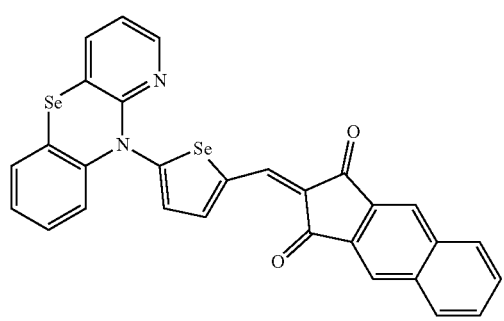
[Group 3]

-continued
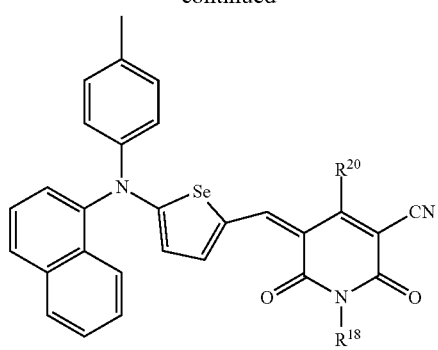
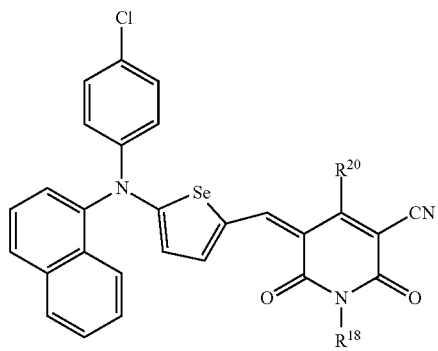
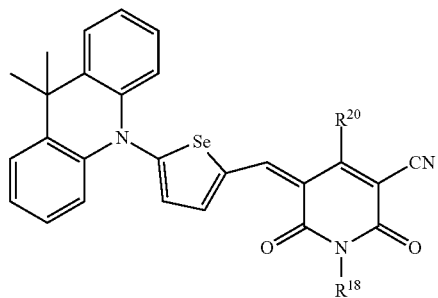
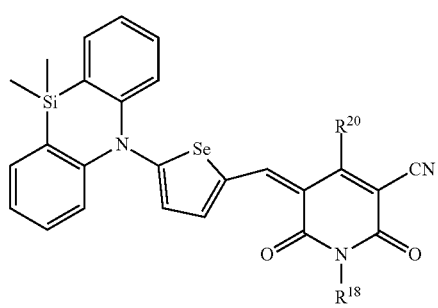
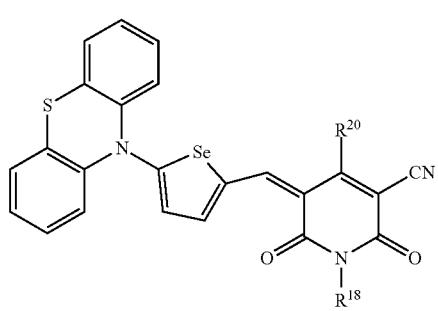
-continued
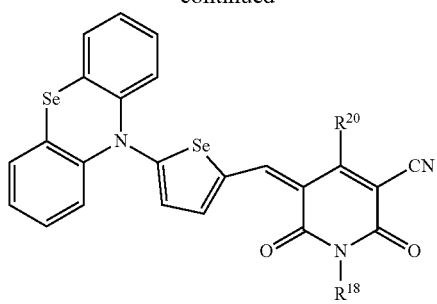
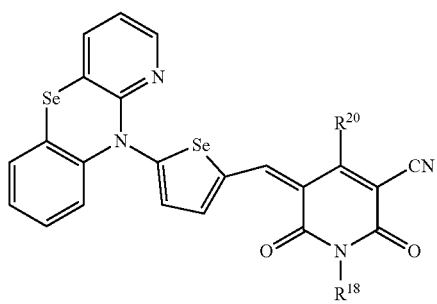
[Group 4]
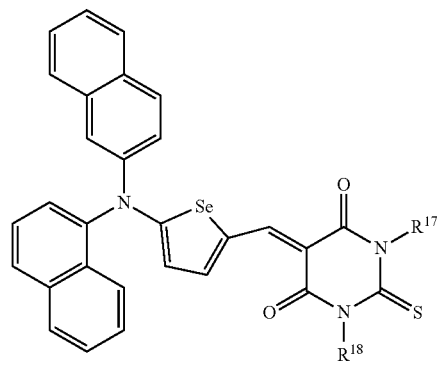
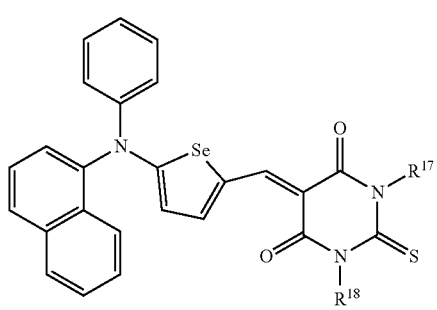
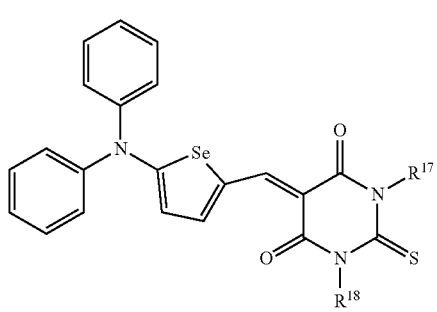

31
-continued

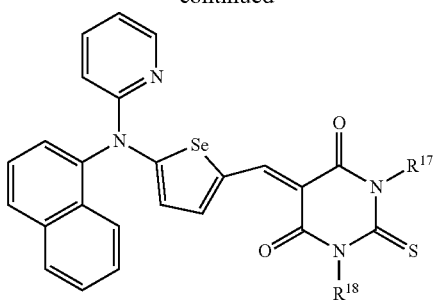

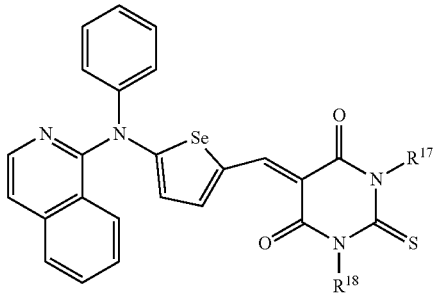

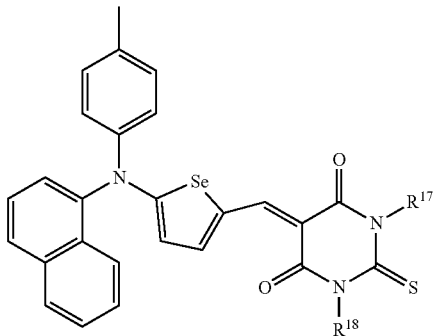

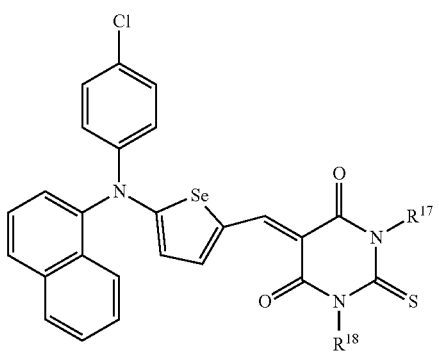

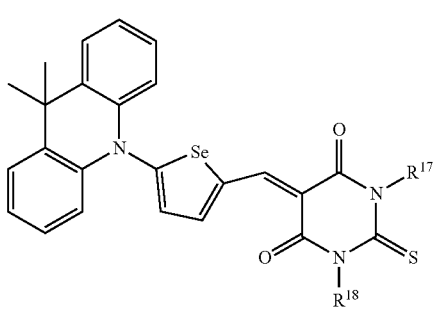

32
-continued

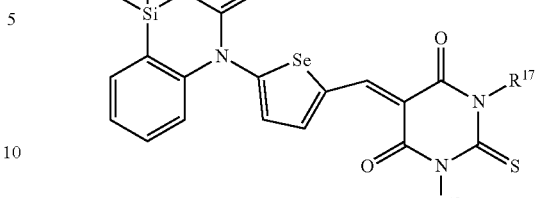

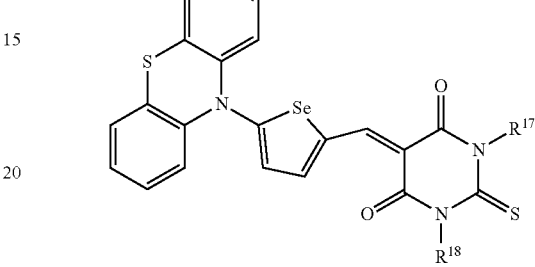

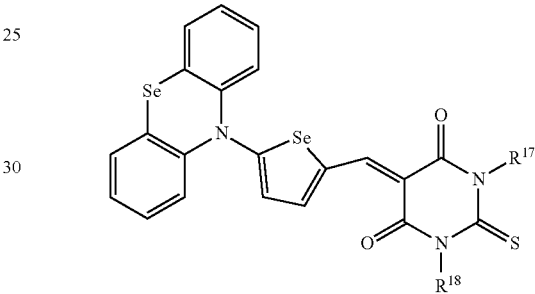

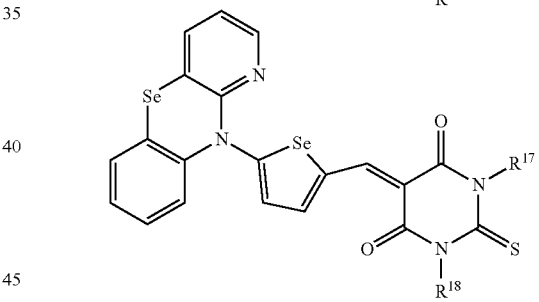

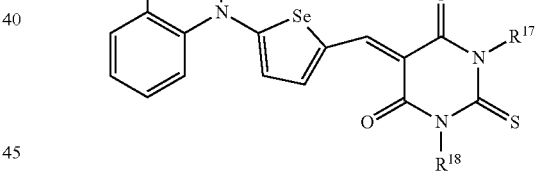

In Groups 1 to 4,
hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof, and $R^{16}$, $R^{17}$, $R^{18}$, $R^{20}$, and $R^f$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof.

The n-type semiconductor may include the fullerene derivative.

The fullerene derivative may electrically match with the p-type semiconductor effectively and may have for example a LUMO energy level of about 3.7 eV to about 5.0 eV and a HOMO energy level of about 5.8 eV to about 7.0 eV. Within the ranges, for example it may have a LUMO energy level of about 3.8 eV to about 4.9 eV and a HOMO energy level of about 6.0 eV to about 6.9 eV, a LUMO energy level of about 3.8 eV to about 4.8 eV and a HOMO energy level of about 6.0 eV to 6.7 eV, or a LUMO energy level of about 3.8 eV to about 4.5 eV and a HOMO energy level of about 6.0 eV to 6.5 eV. The fullerene derivative may have for example an energy band gap of about 2.0 eV to about 2.3 eV. When the fullerene derivative has an energy level within the ranges, it may play an effective role of an n-type semiconductor with the p-type semiconductor.

The fullerene derivative may be designed as long as it satisfies the electrical characteristics and may be for example represented by Chemical Formula

[Chemical Formula 1]

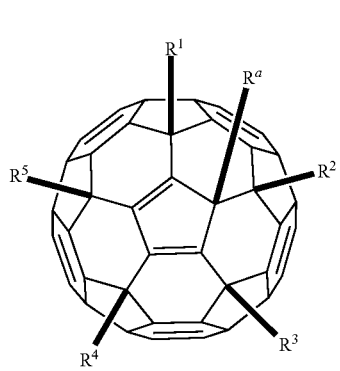

In Chemical Formula 1, $R^a$ is hydrogen or a C1 to C10 alkyl group, $R^1$ to $R^5$ are independently a substituted or unsubstituted C1 to C10 alkyl group or a substituted or unsubstituted C6 to C12 aryl group, and at least one of $R^1$ to $R^5$ is a C1 to C10 alkyl group substituted with a fluorine, a cyano group, or a combination thereof or a C6 to C12 aryl group substituted with a fluorine, a cyano group, or a combination thereof.

For example, $R^1$ to $R^5$ of Chemical Formula 1 may independently be a C1 to C10 alkyl group substituted with a fluorine, a cyano group, or a combination thereof or a C6 to C12 aryl group substituted with a fluorine, a cyano group, or a combination thereof.

For example, $R^1$ to $R^5$ of Chemical Formula 1 may independently be an alkyl group substituted with one fluorine, a phenyl group substituted with one fluorine, a biphenyl group substituted with one fluorine, or a naphthyl group substituted with one fluorine.

For example, $R^1$ to $R^5$ of Chemical Formula 1 may independently be an alkyl group substituted with two fluorines, a phenyl group substituted with two fluorines, a biphenyl group substituted with two fluorines, or a naphthyl group substituted with two fluorines.

For example, $R^1$ to $R^5$ of Chemical Formula 1 may independently be an alkyl group substituted with three fluorines, a phenyl group substituted with three fluorines, a biphenyl group substituted with three fluorines, or a naphthyl group substituted with three fluorines.

For example, $R^1$ to $R^5$ of Chemical Formula 1 may independently be an alkyl group substituted with four fluorines, a phenyl group substituted with four fluorines, a biphenyl group substituted with four fluorines, or a naphthyl group substituted with four fluorines.

For example, $R^1$ to $R^5$ of Chemical Formula 1 may independently be an alkyl group substituted with five fluorines, a phenyl group substituted with five fluorines, a biphenyl group substituted with five fluorines, or a naphthyl group substituted with five fluorines.

For example, $R^1$ to $R^5$ of Chemical Formula 1 may independently be an alkyl group substituted with one cyano group, a phenyl group substituted with one cyano group, a biphenyl group substituted with one cyano group, or a naphthyl group substituted with one cyano group.

For example, $R^1$ to $R^5$ of Chemical Formula 1 may independently be an alkyl group substituted with two cyano groups, a phenyl group substituted with two cyano groups, a biphenyl group substituted with two cyano groups, or a naphthyl group substituted with two cyano groups.

For example, $R^1$ to $R^5$ of Chemical Formula 1 may independently be an alkyl group substituted with three cyano groups, a phenyl group substituted with three cyano groups, a biphenyl group substituted with three cyano groups, or a naphthyl group substituted with three cyano groups.

For example, $R^1$ to $R^5$ of Chemical Formula 1 may independently be an alkyl group substituted with four cyano groups, a phenyl group substituted with four cyano groups, a biphenyl group substituted with four cyano groups, or a naphthyl group substituted with four cyano groups.

For example, $R^1$ to $R^5$ of Chemical Formula 1 may independently be an alkyl group substituted with five cyano groups, a phenyl group substituted with five cyano groups, a biphenyl group substituted with five cyano groups, or a naphthyl group substituted with five cyano groups.

The fullerene derivative may be for example represented by one chemical formula of Chemical Formulae 1a to 1l, but is not limited thereto.

[Chemical Formula 1a]

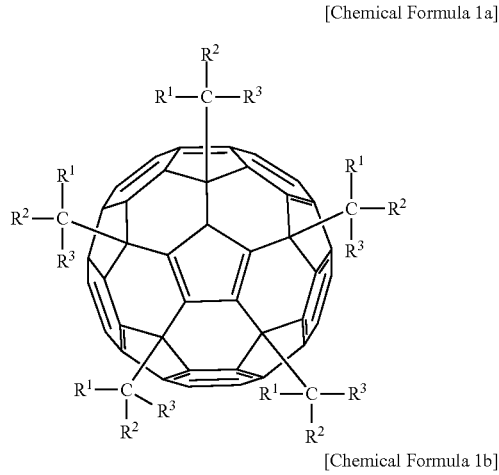

[Chemical Formula 1b]

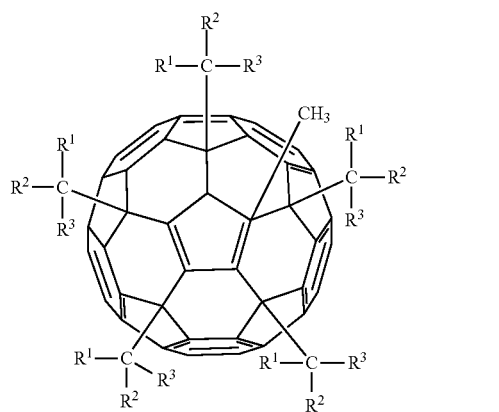

-continued
[Chemical Formula 1c]
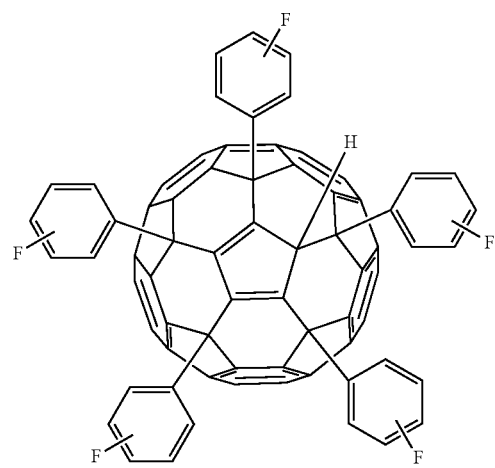
[Chemical Formula 1d]
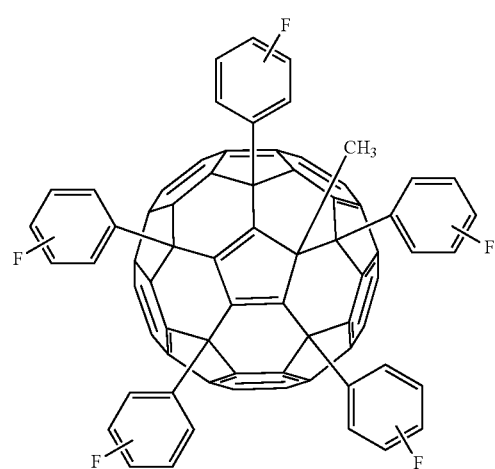
[Chemical Formula 1e]
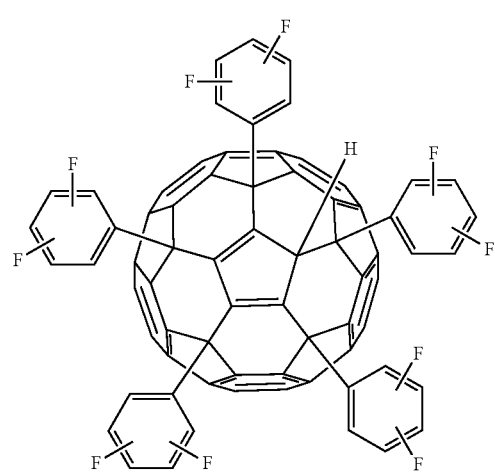
[Chemical Formula 1f]
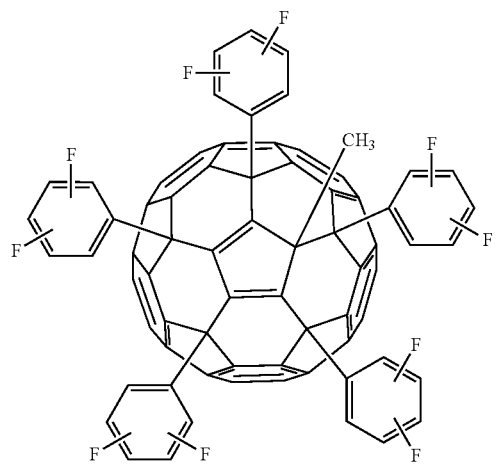
[Chemical Formula 1g]
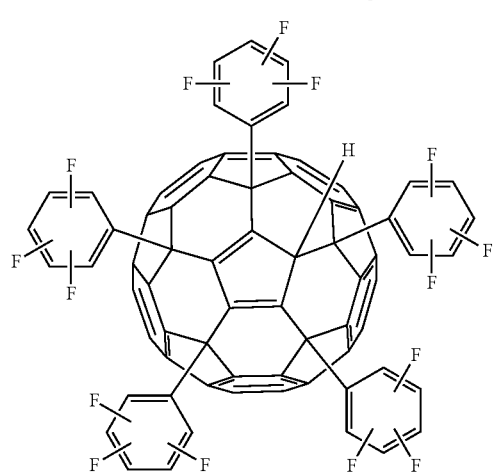
[Chemical Formula 1h]
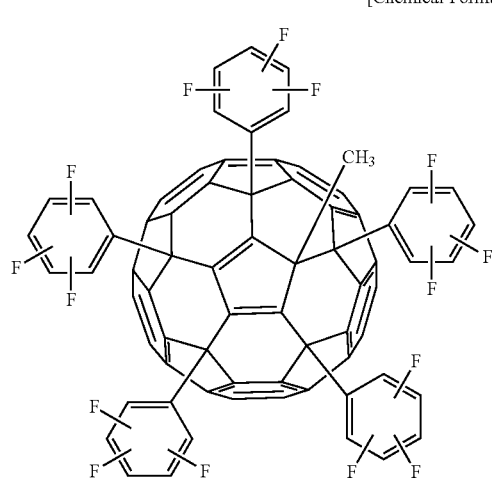

[Chemical Formula 1i]

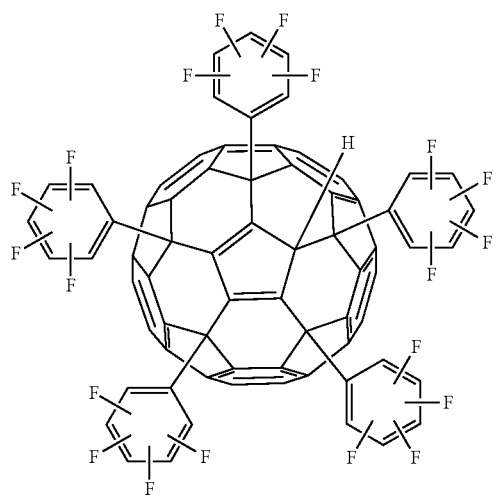

[Chemical Formula 1j]

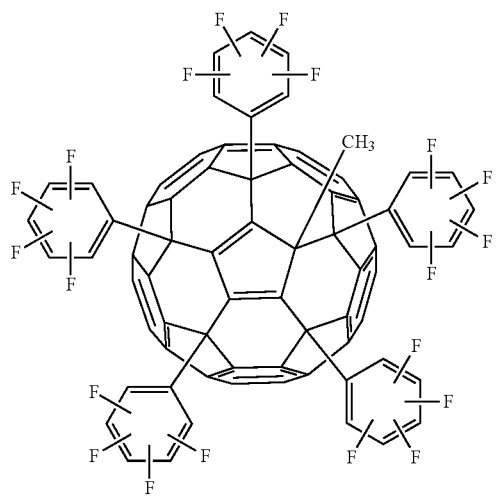

[Chemical Formula 1k]

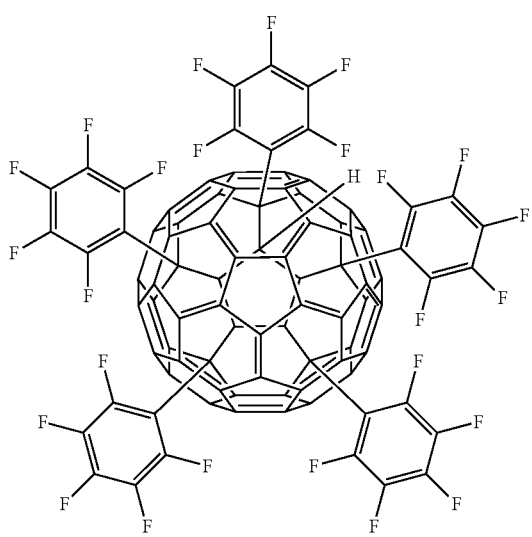

[Chemical Formula 1l]

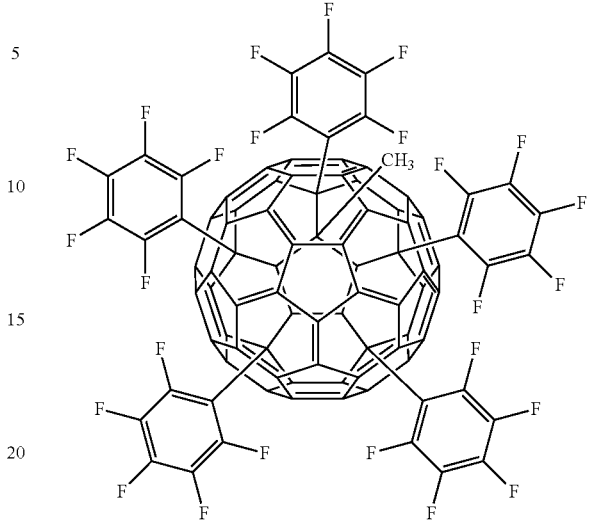

In Chemical Formulae 1a and 1b, $R^1$ to $R^3$ is hydrogen or a fluorine and at least one of $R^1$ to $R^3$ is a fluorine.

The fullerene derivative is effectively electrically matched with the p-type semiconductor as aforementioned. In addition, the fullerene derivative has a 5-substituted or 6-substituted structure at a particular position and thus may increase a steric hindrance but decrease a pi conjugation structure compared with the unsubstituted C60 fullerene. Accordingly, the fullerene derivative may suppress an aggregation during the deposition compared with the unsubstituted C60 fullerene and thus may improve deposition characteristics and reduce optical properties such as a shift of an absorption wavelength spectrum of light which may be caused by the aggregation.

The above p-type semiconductor and an n-type semiconductor including the fullerene derivative may be configured to be co-deposited through ("based on") sublimation to form ("at least partially comprise") an active layer, and thus the active layer may maintain ("may be configured to maintain") inherent characteristics of the fullerene derivative without breaking and/or transforming a chemical bond of the fullerene derivative during the co-deposition.

The fullerene derivative may have optical absorption characteristics shifted toward a short wavelength compared with the unsubstituted C60 fullerene, for example, a peak absorption wavelength ($\lambda_{max}$) of the thin film including the fullerene derivative may be shorter than that of the thin film including the unsubstituted C60 fullerene.

Optical absorption characteristics of the active layer may be expressed by combining those of the p-type semiconductor with those of the n-type semiconductor. For example, an absorption peak of an active layer including a p-type semiconductor selectively absorbing light in a wavelength spectrum of light of about 500 nm to about 600 nm and an n-type semiconductor including a fullerene derivative may be easily separated compared with that the thin film including the p-type semiconductor selectively absorbing light in a wavelength spectrum of light of about 500 nm to about 600 nm and an unsubstituted C60 fullerene, and thus wavelength selectivity of the active layer may be increased. Accordingly, the active layer may be effectively used for a photoelectric device requiring the wavelength selectivity.

The active layer may include an intrinsic layer formed based on co-depositing the p-type semiconductor and the n-type semiconductor including the fullerene derivative and the p-type semiconductor and the n-type semiconductor may be included in a volume ratio of about 1:9 to about 9:1, for example about 2:8 to about 8:2, about 3:7 to about 7:3, about 4:6 to about 6:4, or about 5:5.

The active layer may further include a p-type layer and/or an n-type layer in addition to the intrinsic layer. The p-type layer may include the p-type semiconductor and the n-type layer may include the n-type semiconductor. For example, the active layer may include various combinations of a p-type layer/an l layer, an l layer/an n-type layer, a p-type layer/an l layer/a n-type layer, and the like.

The organic layer 30 may further include a charge auxiliary layer (not shown) between the first electrode 10 and the active layer and/or between the second electrode 20 and the active layer.

The charge auxiliary layer may make holes and electrons separated in the organic layer 30 (e.g., active layer) be transported easily to improve efficiency.

The charge auxiliary layer may include at least one selected from a hole injection layer for facilitating hole injection, a hole transport layer for facilitating hole transport, an electron blocking layer for preventing electron transport, an electron injection layer for facilitating electron injection, an electron transport layer for facilitating electron transport, and a hole blocking layer for preventing hole transport.

The charge auxiliary layer may include for example an organic material, an inorganic material, or an organic/inorganic material. The organic material may be an organic material having hole or electron characteristics and the inorganic material may be for example a metal oxide such as molybdenum oxide, tungsten oxide, or nickel oxide.

The charge auxiliary layer may include for example the fullerene derivative.

The photoelectric device 100 may further include an anti-reflection layer (not shown) on one surface of the first electrode 10 or the second electrode 20. The anti-reflection layer is disposed at a light incidence side and lowers reflectance of light of incident light and thereby light absorbance is further improved. For example, when light enters from the first electrode 10, the anti-reflection layer may be disposed on the first electrode 10 while when light enters from the second electrode 20, the anti-reflection layer may be disposed under the second electrode 20.

The anti-reflection layer may include, for example a material having a refractive index of about 1.6 to about 2.5, and may include for example at least one of a metal oxide, a metal sulfide, and an organic material having a refractive index within the ranges. The anti-reflection layer may include, for example a metal oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganese-containing oxide, a chromium-containing oxide, a tellurium-containing oxide, or a combination thereof; a metal sulfide such as zinc sulfide; or an organic material such as an amine derivative, but is not limited thereto.

In the photoelectric device 100, when light enters from the first electrode 10 or second electrode 20 and the organic layer 30 (e.g., active layer) absorbs light in a predetermined wavelength spectrum of light, excitons may be produced from the inside. The excitons are separated into holes and electrons in the organic layer 30 (e.g., active layer), and the separated holes are transported to an anode that is one of the first electrode 10 and the second electrode 20 and the separated electrons are transported to the cathode that is the other of and the first electrode 10 and the second electrode 20 so as to flow a current.

The photoelectric device 100 may be applied to ("included in") a solar cell, an image sensor, a photodetector, a photosensor, and an organic light emitting diode (OLED), but is not limited thereto.

The photoelectric device may be for example applied to an image sensor.

Hereinafter, an example of an image sensor including the photoelectric device is described referring to drawings. As an example of an image sensor, an organic CMOS image sensor is described.

Figure 2:
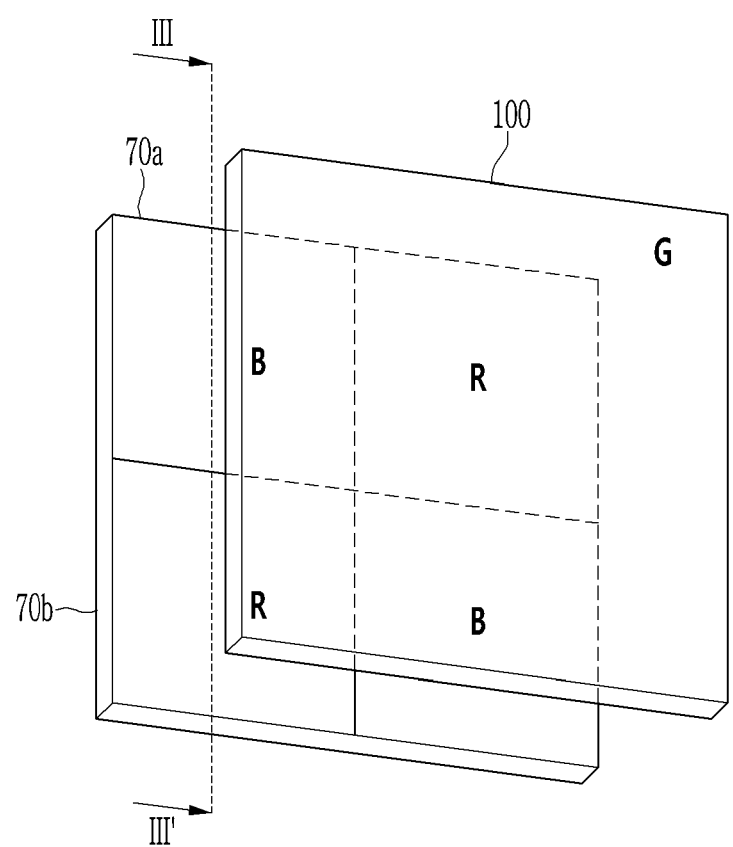
FIG. 2 is a schematic top plan view showing an organic CMOS image sensor according to some example embodiments.
Figure 3:
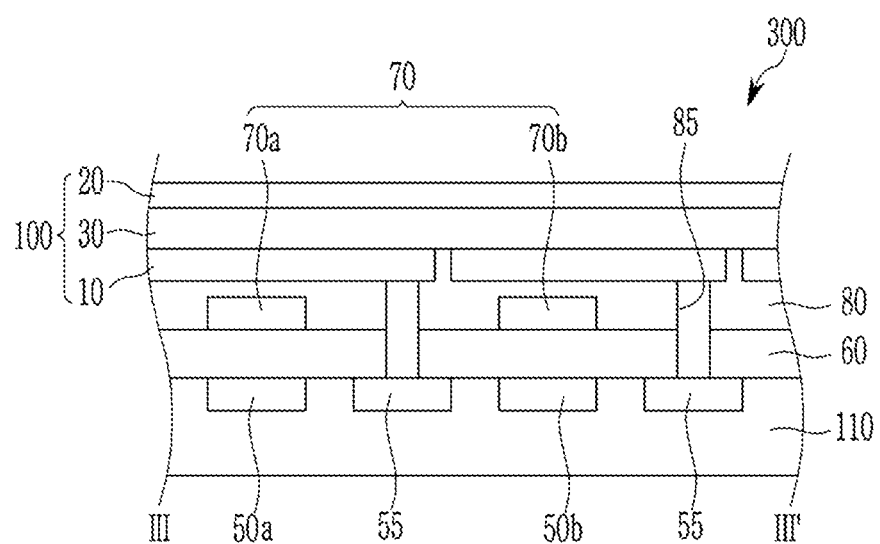
FIG. 3 is a cross-sectional view showing one example of the organic CMOS image sensor of FIG. 2.

FIG. 2 is a schematic top plan view of an organic CMOS image sensor according to some example embodiments and FIG. 3 is a cross-sectional view showing one example of the organic CMOS image sensor of FIG. 2 along cross-sectional view line III-III'.

Referring to FIGS. 2 and 3, an organic CMOS image sensor 300 according to some example embodiments includes a semiconductor substrate 110 integrated with photo-sensing devices 50a and 50b, a transmission transistor (not shown) and a charge storage 55, a lower insulation layer 60, a color filter layer 70, an upper insulation layer 80, and a photoelectric device 100. As referred to herein, a first element that is "integrated with" one or more second elements refers to a first element that defines a volume space wherein the second element(s) is wholly enclosed, such that the first element partially or entirely encloses the second element within the interior of the first element, or partially enclosed, such that the one or more exposed surfaces of the second element, exposed by the first element, are coplanar or define a continuous surface with one or more outer surfaces of the first element.

The semiconductor substrate 110 may be a silicon substrate, and is integrated with the photo-sensing devices 50a and 50b, the transmission transistor (not shown), and the charge storage 55. The photo-sensing devices 50a and 50b may be photodiodes (also referred to herein as "photo-sensing devices").

The photo-sensing devices 50a and 50b, the transmission transistor, and/or the charge storage 55 may be integrated in each pixel, and as shown in the drawing, the photo-sensing devices 50a and 50b may be respectively included in a blue pixel and a red pixel and the charge storage 55 may be included in a green pixel.

The photo-sensing devices 50a and 50b sense ("are configured to sense") light, the information sensed by the photo-sensing devices may be transferred by the transmission transistor, the charge storage 55 is electrically connected to the photoelectric device 100 (e.g., an organic photoelectric device) that will be described later, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing device 50a and 50b.

The lower insulation layer 60 is formed on the metal wire and the pad. The lower insulation layer 60 may be made of ("may at least partially comprise") an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70a formed in a blue pixel and a red filter 70b in a red pixel. In some example embodiments, a green filter is not included, but a green filter may be further included. It will be understood that a blue filter 70a is a filter configured to selectively filter light in a blue wavelength spectrum out of light received at the filter, a red filter 70b is a filter configured to selectively filter light in a red wavelength spectrum out of light received at the filter, and a green filter is a filter configured to selectively filter light in a green wavelength spectrum out of light received at the filter.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The photoelectric device 100 is formed on the upper insulation layer 80. The photoelectric device 100 includes the first electrode 10, the organic layer 30 (e.g., active layer), and the second electrode 20 as described above. In the drawing of FIG. 3, the first electrode 10, the organic layer 30, and the second electrode 20 are sequentially stacked, but this disclosure is not limited thereto, and for example they may be stacked in an order of the second electrode 20, the organic layer 30, and the first electrode 10.

The first electrode 10 and the second electrode 20 may be all light-transmitting electrodes and the organic layer 30 is the same as described above. The organic layer 30 may for example selectively absorb light in a green wavelength spectrum of light and may replace a color filter of a green pixel.

Light in a green wavelength spectrum of light that enters from the second electrode 20 is mainly absorbed by the organic layer 30 and photoelectrically converted and light in a remaining wavelength spectrum of light is transmitted through the first electrode 10 and is sensed by the photo-sensing devices 50a and 50b.

Focusing lens (not shown) may be further formed on the photoelectric device 100. The focusing lens may control a direction of incident light and gather the light in one region. The focusing lens may have a shape of, for example, a cylinder or a hemisphere, but is not limited thereto.

As described above, the photoelectric device 100 has a stack structure thereby a size of an image sensor may be reduced to realize a down-sized image sensor.

In addition, the organic layer includes the aforementioned fullerene derivative having optical absorption characteristics shifted toward a short wavelength as described above and thus may increase wavelength selectivity compared with the one including the unsubstituted C60 fullerene.

The photoelectric device selectively absorbing light ("configured to selectively absorb light") in a green wavelength spectrum of light is for example stacked but this disclosure is not limited thereto. For example, a photoelectric device selectively absorbing light in a blue wavelength spectrum of light may be stacked and a green photo-sensing device and a red photo-sensing device may be integrated in the semiconductor substrate 110 or a photoelectric device selectively absorbing light in a red wavelength spectrum of light may be stacked and a green photo-sensing device and a blue photo-sensing device may be integrated in the semiconductor substrate 110.

Figure 4:
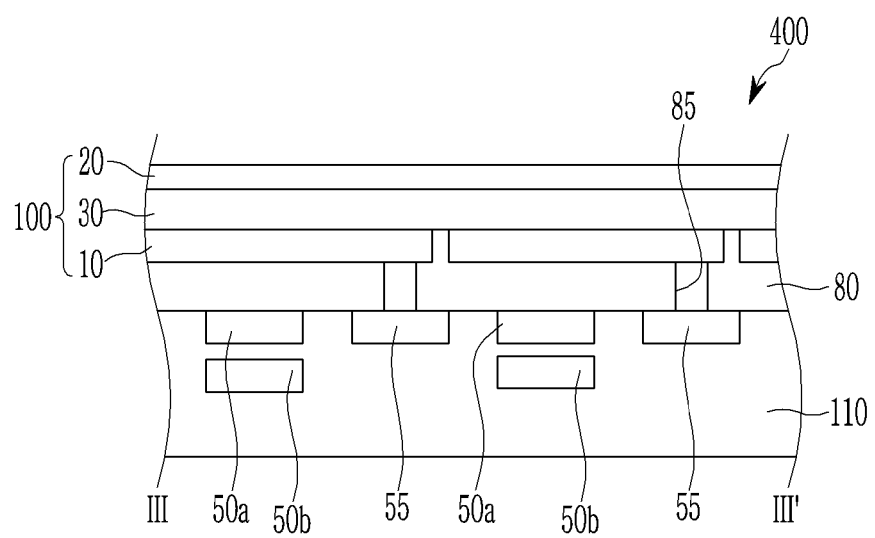
FIG. 4 is a cross-sectional view showing another example of the organic CMOS image sensor.

FIG. 4 is a cross-sectional view showing another example of the organic CMOS image sensor.

The organic CMOS image sensor 400 according to some example embodiments like the above embodiment includes a semiconductor substrate 110 integrated with photo-sensing devices 50a and 50b, a transmission transistor (not shown), and a charge storage 55, an upper insulation layer 80 having a through-hole 85, and a photoelectric device 100.

However, in the organic CMOS image sensor 400 according to some example embodiments unlike the above embodiment, the photo-sensing devices 50a and 50b are stacked in a vertical direction (e.g., the photo-sensing devices 50a and 50b vertically overlap with respect to each other), but the color filter layer 70 is omitted. The photo-sensing devices 50a and 50b are electrically connected to charge storage (not shown) and signal may be transferred by the transmission transistor. The photo-sensing devices 50a and 50b may selectively absorb light in each wavelength spectrum of light depending on a stacking depth.

Focusing lens (not shown) may be further formed on the photoelectric device 100. The focusing lens may control a direction of incident light and gather the light in one region. The focusing lens may have a shape of, for example, a cylinder or a hemisphere, but is not limited thereto.

As described above, the photoelectric device selectively absorbing light in a green wavelength spectrum of light is stacked and the red photo-sensing device and the blue photo-sensing device are stacked, and thereby a size of an image sensor may be reduced to realize a down-sized image sensor.

In FIG. 4, the photoelectric device selectively absorbing light ("configured to selectively absorb light") in a green wavelength spectrum of light is for example stacked, but this disclosure is not limited thereto. For example, a photoelectric device selectively absorbing light in a blue wavelength spectrum of light may be stacked and a green photo-sensing device and a red photo-sensing device may be integrated in the semiconductor substrate 110 or a photoelectric device selectively absorbing light ("configured to selectively absorb light") in a red wavelength spectrum of light may be stacked and a green photo-sensing device and a blue photo-sensing device may be integrated in the semiconductor substrate 110.

Figure 5:
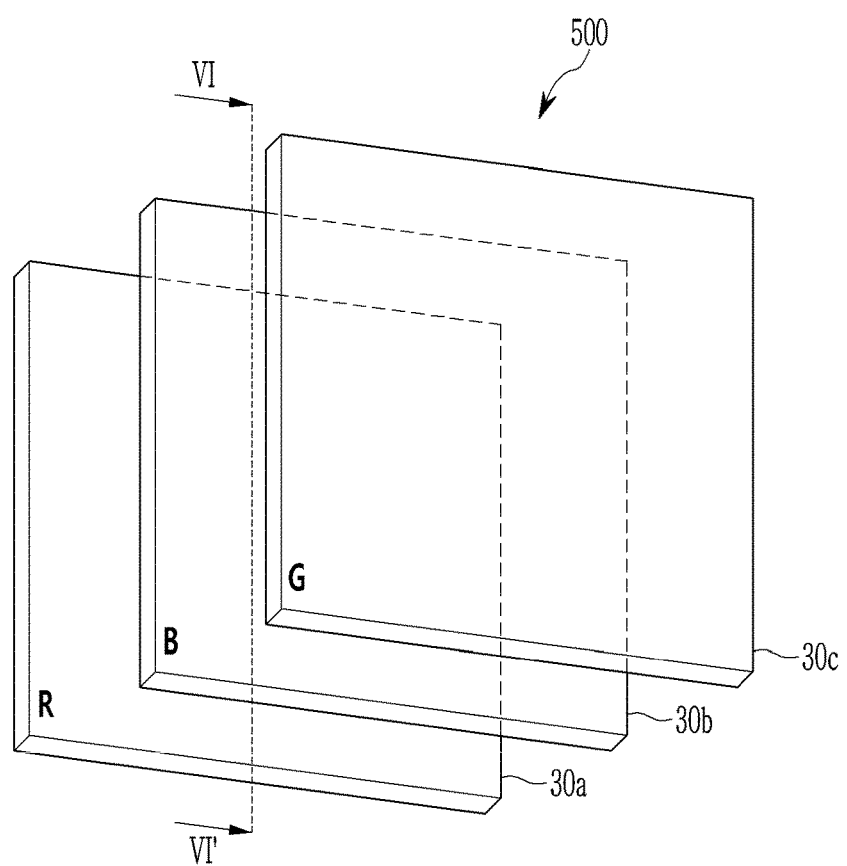
FIG. 5 is a schematic top plan view showing an organic CMOS image sensor according to some example embodiments.
Figure 6:
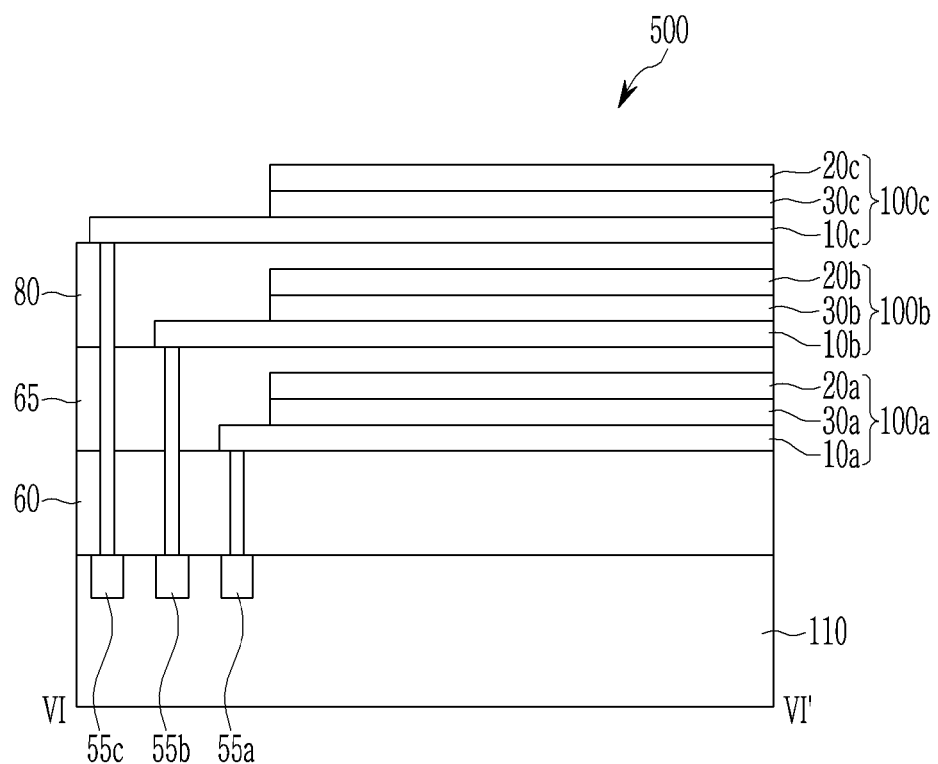
FIG. 6 is a cross-sectional view showing one example of the organic CMOS image sensor of FIG. 5.

FIG. 5 is a schematic top plan view showing an organic CMOS image sensor according to some example embodiments and FIG. 6 is a cross-sectional view of the organic CMOS image sensor of FIG. 5 along cross-sectional view line VI-VI'.

The organic CMOS image sensor 500 according to some example embodiments includes a photoelectric device selectively absorbing light ("configured to selectively absorb light") in a green wavelength spectrum of light, a photoelectric device selectively absorbing light ("configured to selectively absorb light") in a blue wavelength spectrum of light, and a photoelectric device selectively absorbing light ("configured to selectively absorb light") in a red wavelength spectrum of light that are stacked.

The organic CMOS image sensor 500 according to some example embodiments includes a semiconductor substrate 110, a lower insulation layer 60, an intermediate insulation layer 65, an upper insulation layer 80, a first photoelectric device 100a, a second photoelectric device 100b, and a third photoelectric device 100c.

The semiconductor substrate 110 may be a silicon substrate, and is integrated with the transmission transistor (not shown) and the charge storages 55a, 55b, and 55c.

A metal line (not shown) and pad (not shown) are formed on the semiconductor substrate 110 and a lower insulation layer 60 is formed on the metal line and pad.

The first photoelectric device 100a is formed on the lower insulation layer 60.

The first photoelectric device 100a includes a first electrode 10a and a second electrode 20a facing each other and an organic layer 30a disposed between the first electrode 10a and the second electrode 20a. The first electrode 10a, the second electrode 20a, and the organic layer 30a are the same as described above and the organic layer 30a may selectively absorb light in one wavelength spectrum of light of red, blue and green wavelength spectra of light. For example, the first photoelectric device 100a may be a red photoelectric device (e.g., configured to selectively absorb red light).

In the drawing, the first electrode 10a, the organic layer 30a, and the second electrode 20a are sequentially stacked, but this disclosure is not limited thereto, and for example they may be stacked in an order of the second electrode 20a, the organic layer 30a, and the first electrode 10a.

The intermediate insulation layer 65 is formed on the first photoelectric device 100a.

The second photoelectric device 100b is formed on the intermediate insulation layer 65.

The second photoelectric device 100b includes a first electrode 10b and a second electrode 20b facing each other and an organic layer 30b disposed between the first electrode 10b and the second electrode 20b. The first electrode 10b, the second electrode 20b, and the organic layer 30b are the same as described above and the organic layer 30b may selectively absorb light in one wavelength spectrum of light of red, blue and green. For example, the second photoelectric device 100b may be a blue photoelectric device.

In the drawing, the first electrode 10b, the organic layer 30b, and the second electrode 20b are sequentially stacked, but this disclosure is not limited thereto, and for example they may be stacked in an order of the second electrode 20b, the organic layer 30b, and the first electrode 10b.

The upper insulation layer 80 is formed on the second photoelectric device 100b. The lower insulation layer 60, the intermediate insulation layer 65, and the upper insulation layer 80 have a plurality of through-holes exposing the charge storages 55a, 55b, and 55c.

The third photoelectric device 100c is formed on the upper insulation layer 80. The third photoelectric device 100c includes a first electrode 10c and a second electrode 20c facing each other and an organic layer 30c disposed between the first electrode 10c and the second electrode 20c. The first electrode 10c, the second electrode 20c, and the organic layer 30c are the same as described above and the organic layer 30c may selectively absorb light in one wavelength spectrum of light of red, blue and green. For example, the third photoelectric device 100c may be a green photoelectric device.

In the drawing, the first electrode 10c, the organic layer 30c, and the second electrode 20c are sequentially stacked, but this disclosure is not limited thereto, and for example they may be stacked in an order of the second electrode 20c, the organic layer 30c, and the first electrode 10c.

Focusing lens (not shown) may be further formed on the photoelectric device 100c. The focusing lens may control a direction of incident light and gather the light in one region. The focusing lens may have a shape of, for example, a cylinder or a hemisphere, but is not limited thereto.

In the drawing, the first photoelectric device 100a, the second photoelectric device 100b, and the third photoelectric device 100c are sequentially stacked, but the present disclosure is not limited thereto, and they may be stacked in various orders.

As described above, the first photoelectric device 100a, the second photoelectric device 100b, and the third photoelectric device 100c that absorb light in different wavelength spectra of light are stacked, and thereby a size of an image sensor may be reduced to realize a down-sized image sensor.

The image sensor may be applied to ("included in"), for example, various electronic devices such as a mobile phone or a digital camera, but is not limited thereto.

Hereinafter, the embodiments are illustrated in more detail, as shown in at least FIGS. 7-8, with reference to one or more examples. However, these examples are simply examples, and the scope of claims is not limited thereto.

SYNTHESIS EXAMPLES

Synthesis Example 1

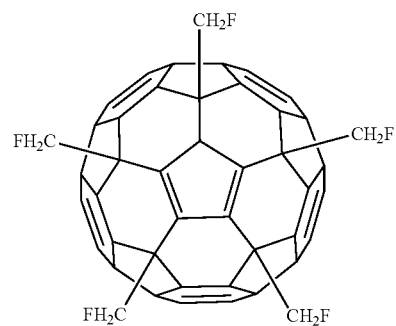

[Chemical Formula 1aa]

1.8 g of C60(CH$_2$TMS)$_5$H is synthesized according to the same method as a method described in Organic Syntheses, Vol. 83, p. 80-87 (2006) except for using 2.0 g of fullerene C60 and (trimethylsilyl)methyl magnesium chloride instead of methyl magnesium bromide under a nitrogen atmosphere. A separation yield of C60(CH$_2$TMS)$_5$H is 80%.

Subsequently, 1.0 g of the obtained C60(CH$_2$TMS)$_5$H is dissolved in 100 ml of tetrahydrofuran (THF) under a nitrogen atmosphere, 5.5 equivalents of t-BuLi is reacted with the solution at −70° C., and then, a fluoridation (F) of an α position of a silyl group is performed by adding 6.0 equivalents of N-fluorobenzenesulfonimide, while a desylilation is simultaneously performed by stopping the reaction under an acid condition. Subsequently, after distilling the THF, and then, a lithium salt and the like remaining there are removed through silica gel using dimethylsulfide (CS$_2$) as a developing solvent. Subsequently, after distilling the developing solvent, a HPLC is performed by using toluene and isopropanol (=7:3 (v/v)) as a developing solvent in a Buckyprep-column to obtain 0.5 g of C60(CH$_2$F)$_5$H represented by Chemical Formula 1aa. A separation yield of the obtained C60(CH$_2$F)$_5$H is 70%.

$^1$H NMR (500 MHz, CS$_2$/CDCl$_3$=2/1): δ 2.39 (s, 6H), 2.46 (s, 6H), 2.61 (s, 3H), 4.52 (s, 1H)

Synthesis Example 2

[Chemical Formula 1ca]

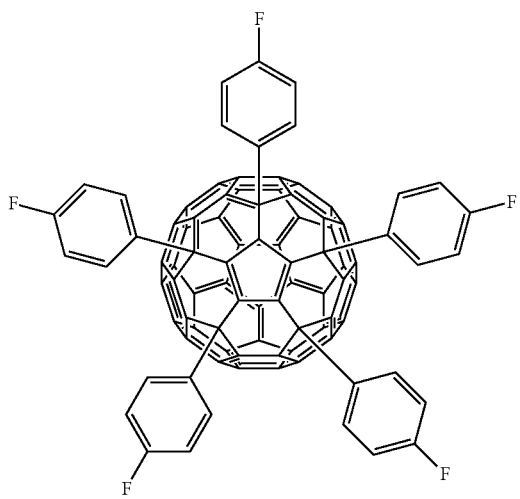

1.6 g of C60(C$_6$H$_5$F)$_5$H represented by Chemical Formula 1ca is synthesized according to the same method as a method described in J. Organometa. Chem. 599, 32 (2000) except for using 1.0 g of fullerene C60 and 4-fluorophenyl magnesium bromide instead of phenyl magnesium bromide (PhMgBr) under a nitrogen atmosphere. A separation yield of the obtained C60(C$_6$H$_5$F)$_5$H is 97%.

$^1$H NMR (500 MHz, CS$_2$/CDCl$_3$=2/1): δ 7.87-7.85 (m, 5H), 7.62-7.60 (m, 10H), 7.44-7.42 (m, 5H), 5.19 (s, 1H).

Synthesis Example 3

[Chemical Formula 1da]

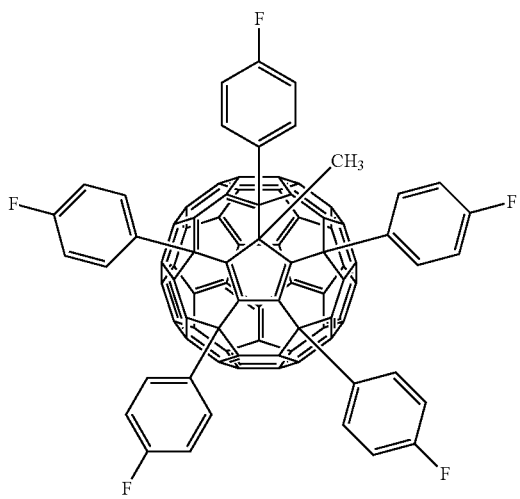

0.3 g of C60(C$_6$H$_5$F)$_5$H is added to 80 ml of THF under a nitrogen atmosphere, 0.3 ml of a THF solution (1N) of 1.3 equivalents of potassium t-butoxide (KOtBu) is added thereto, and the obtained mixture is stirred for 30 minutes at room temperature. Subsequently, 4.7 ml of 300 equivalents of methyl iodide is added to the aforementioned solution, and the obtained mixture is stirred for 24 hours. After distilling a solvent therein, a lithium salt and the like are removed through silica gel using CS$_2$ as a developing solvent. Subsequently, the solvent is distilled to obtain 0.2 g of C60(C$_6$H$_5$F)$_5$CH$_3$ Chemical Formula 1da. A separation yield of the obtained C60(C$_6$H$_5$F)$_5$CH$_3$ is 83%.

$^1$H NMR (500 MHz, CS$_2$/CDCl$_3$=2/1): δ 7.87-7.85 (m, 5H), 7.62-7.60 (m, 10H), 7.44-7.42 (m, 5H), 1.39 (s, 3H).

Synthesis Example 4

[Chemical Formula 1fa]

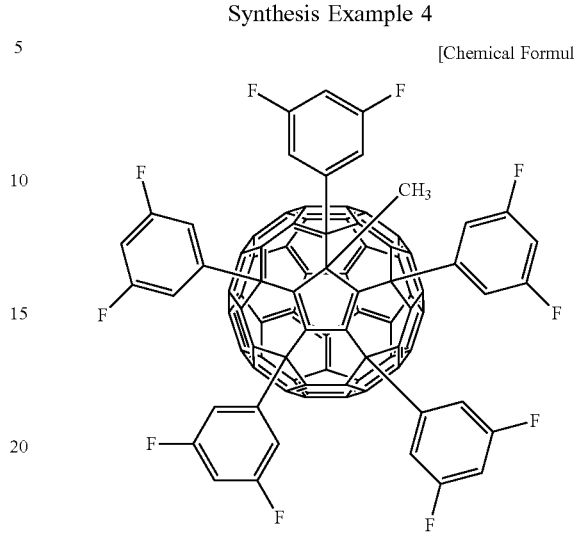

A synthesis is performed according to the same method as a method described in J. Organometa. Chem. 599, 32 (2000) except for using 0.9 g of fullerene C$_{60}$ and a 3,5-difluorophenyl magnesium bromide solution (a 2-THF solution, 0.5N) instead of a 4-fluorophenyl magnesium bromide solution under a nitrogen atmosphere. A product is obtained in an amount of 0.6 g, and a separation yield of the product is 40%.

Subsequently, 0.2 g of a C60(C$_6$H$_3$F$_2$)$_5$CH$_3$ compound represented by Chemical Formula 1fa is obtained according to the same method as Synthesis Example 3 except for using C60(C$_6$H$_3$F$_2$)$_5$H instead of C60(C$_6$H$_5$F)$_5$H. A separation yield of the compound is 80%.

$^1$H NMR (500 MHz, CS$_2$/CDCl$_3$=2/1): δ 7.35-7.10 (m, 4H), 7.05-7.15 (m, 4H), 7.70-7.95 (m, 4H), 1.39 (s, 3H).

Synthesis Example 5

[Chemical Formula 1ha]

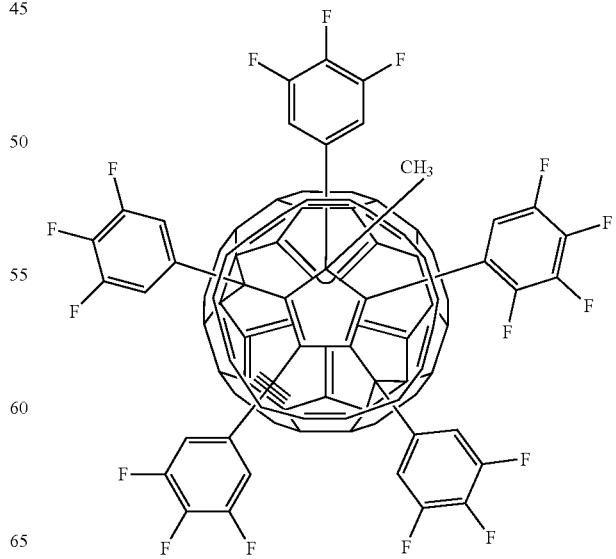

A synthesis is performed according to the same method as a method described in J. Organometa. Chem. 599, 32 (2000) except for using 0.9 g of fullerene $C_{60}$ and a 3,4,5-trifluorophenyl magnesium bromide solution (normality of 0.3, a THF solution) instead of a 4-fluorophenyl magnesium bromide solution under a nitrogen atmosphere. A product is obtained in an amount of 0.6 g, and a separation yield of the product is 36%.

Subsequently, 0.2 g of a $C60(C_6H_2F_3)_5CH_3$ compound represented by Chemical Formula 1ha is obtained according to the same method as Synthesis Example 3 except for using $C60(C_6H_2F_3)_5H$ instead of $C60(C_6H_5F)_5H$. A separation yield of the compound is 70%.

$^1$H NMR (500 MHz, $CS_2/CDCl_3$=2/1): δ 7.05-7.15 (m, 8H), 7.70-7.95 (m, 2H), 1.39 (s, 3H).

Synthesis Example 6

[Chemical Formula 1ha]

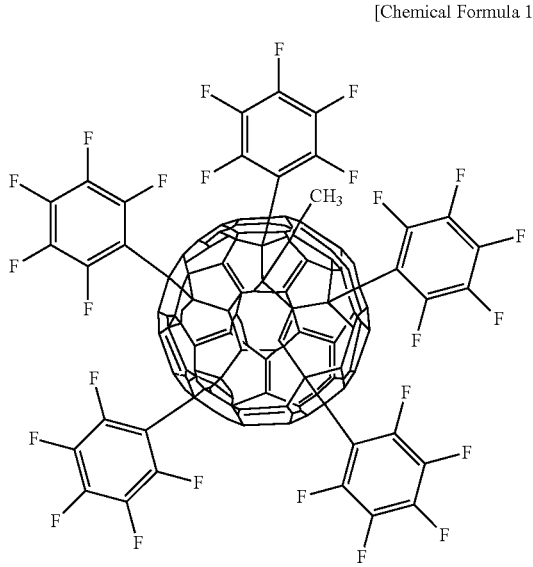

A synthesis is performed according to the same method as a method described in J. Organometa. Chem. 599, 32 2000 except for using 0.9 g of fullerene $C_{60}$ and a 2,3,4,5,6-pentafluorophenylmagnesium bromide solution (0.5N, a diethylether solution) instead of a 4-fluorophenyl magnesium bromide solution under a nitrogen atmosphere. A product is obtained in an amount of 0.6 g, and a separation yield of the product is 30%.

Subsequently, 0.2 g of a $C60(C_6F_5)_5CH_3$ compound represented by Chemical Formula 1la is synthesized according to the same method as Synthesis Example 3 except for using $C60(C_6F_5)_5H$ instead of $C60(C_6H_5F)_5H$. A separation yield of the compound is 60%.

$^1$H NMR (500 MHz, $CS_2/CDCl_3$=2/1): δ 1.39 (s, 3H).

Comparative Synthesis Example 1

[Chemical Formula A]

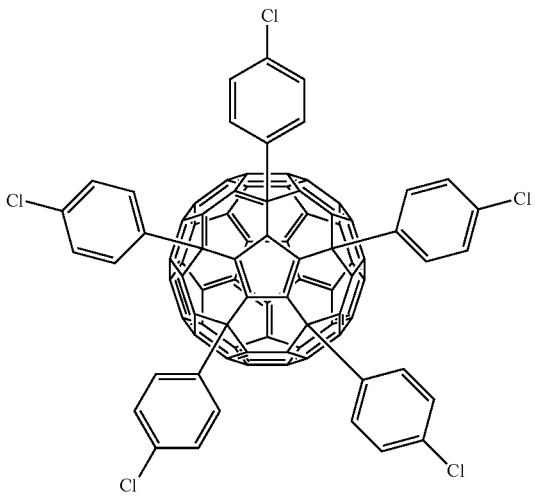

0.6 g of $C60(C_6H_5Cl)_5H$ represented by Chemical Formula A is obtained according to the same method as a method described in J. Organometa. Chem. 599, 32 (2000) except for using 0.9 g of fullerene C60 under a nitrogen atmosphere. A separation yield of the compound is 30%.

Data of $^1$H NMR perfectly correspond with those described in J. Organometa. Chem. 599, 32 (2000).

Comparative Synthesis Example 2

[Chemical Formula B]

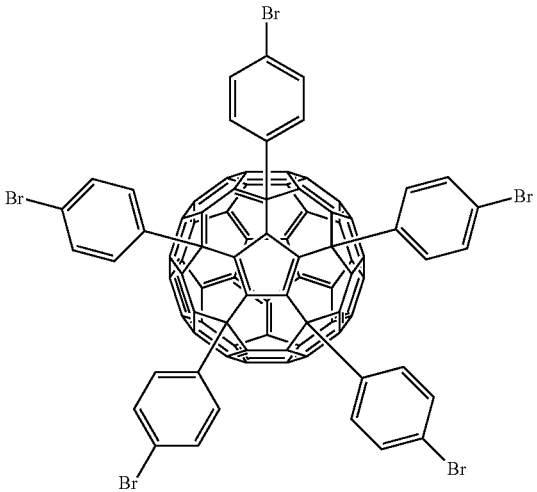

0.6 g of $C60(C_6H_5Br)_5H$ represented by Chemical Formula B is obtained according to the same method as a method described in J. Organometa. Chem. 599, 32 (2000) except for using 0.9 g of fullerene C60 under a nitrogen atmosphere. A separation yield of the compound is 30%.

Data of $^1$H NMR perfectly correspond with those which are described in J. Organometa. Chem. 599, 32 (2000).

Comparative Synthesis Example 3

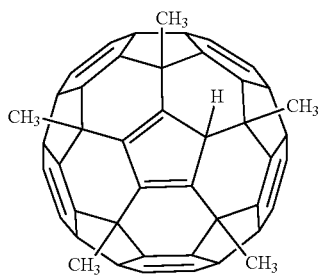
[Chemical Formula C]

2.1 g of C60(CH$_3$)$_5$H represented by Chemical Formula C is obtained under a nitrogen atmosphere according to the same synthesis method as a method described in Organic Syntheses, Vol. 83, p. 80 to 87 (2006) by using 2.0 g of fullerene C60. A separation yield of C60(CH$_3$)$_5$H is 86%.

Data of $^1$H NMR perfectly correspond with those which are described in Organic Syntheses, Vol. 83, p. 80 to 87, 2006.

Comparative Synthesis Example 4

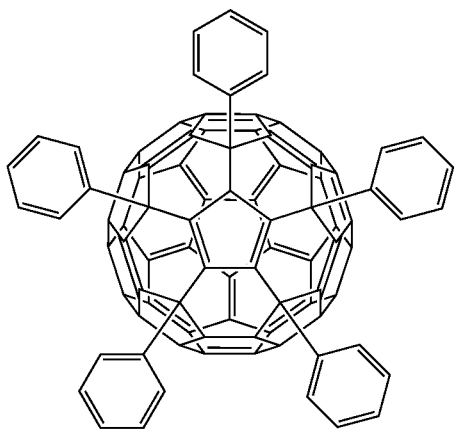
[Chemical Formula D]

0.5 g of C60(C$_6$H$_5$)$_5$H represented by Chemical Formula D is obtained under a nitrogen atmosphere according to the same method as a method described in Journal of Organometallic Chemistry 599, 32 (2000) by using 0.3 g of fullerene C60. A separation yield of C60(C$_6$H$_5$)$_5$H is 94%.

Data of $^1$H NMR perfectly correspond with those which are described in Journal of Organometallic Chemistry 599, 32 (2000).

Comparative Synthesis Example 5

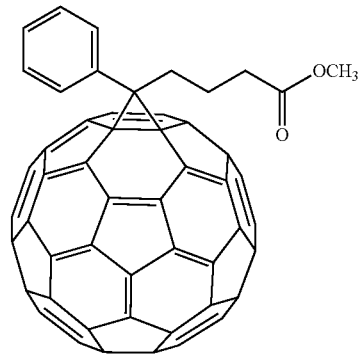
[Chemical Formula E]

A compound represented by Chemical Formula E (Nanom Spectra E102, Frontier Carbon Corporation) is purchased.

Comparative Synthesis Example 6

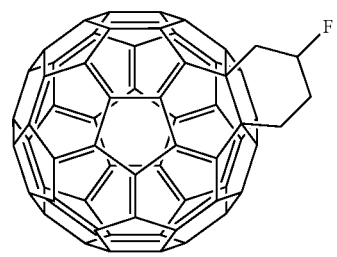
[Chemical Formula F]

1,9-(4-hydroxycyclohexano)buckminster fullerene is synthesized by using 0.3 g of fullerene C60 under a nitrogen atmosphere according to the same method as a method described in J. Org. Chem. 58, 4799 (1993). Subsequently, 0.2 g of a compound represented by Chemical Formula F is obtained by substituting alcohol group into fluorine with Deoxo-Fluor, a general deoxidation fluoridation reagent. A whole yield of the compound is 47%.

$^1$H NMR (500 MHz, CS2/CDCl3=2/1): δ 2.7 (1H), 3.3 (1H), 3.4 (1H), 3.6 (1H), 3.7 (1H0, 3.8 (1H), 5.2 (1H)

Comparative Synthesis Example 7

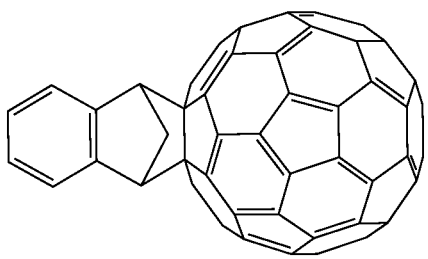
[Chemical Formula G]

A compound represented by Chemical Formula G (Nanom Spectra Q100, Frontier Carbon Corporation) is purchased.

Comparative Synthesis Example 8

[Chemical Formula H]

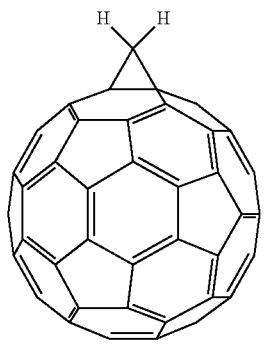

0.2 g of a compound represented by Chemical Formula H is obtained according to the same method as a method described in J. Am. Chem. Soc. 133, 8086 (2011) by using 0.3 g of fullerene C60 under a nitrogen atmosphere. A separation yield is 64%.

Data of $^1$H NMR perfectly correspond with those which are described in J. Am. Chem. Soc. 133, 8086 (2011).

Comparative Synthesis Example 9

[Chemical Formula I]

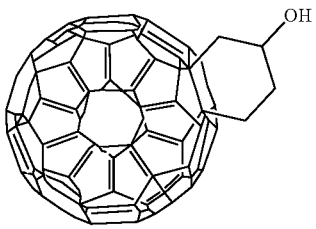

0.2 g of a compound represented by Chemical Formula I is synthesized according to the same method as a method described in J. Org. Chem. 58, 4799 (1993) by using 0.3 g of fullerene C60 under a nitrogen atmosphere. A whole yield of the compound is 55%.

Data of $^1$H NMR perfectly correspond with those which are described in J. Org. Chem. 58, 4799 (1993).

Comparative Synthesis Example 10

[Chemical Formula J]

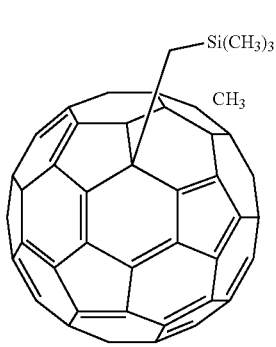

0.3 g of a compound represented by Chemical Formula J is synthesized according to the same method as a method described in J. Am. Chem. Soc. 130, 15430 (2008) by using 0.3 g of fullerene C60 under a nitrogen atmosphere. A separation yield of the compound is 80%.

Data of $^1$H NMR perfectly correspond with those which are described in J. Am. Chem. Soc. 130, 15430 (2008).

Reference Example (Fullerene)

[Chemical Formula K]

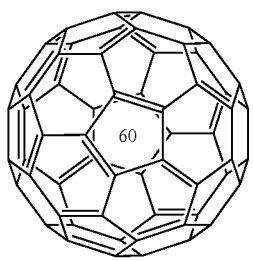

A compound represented by Chemical Formula K (Nanom Purple ST, Frontier Carbon Corporation) is purchased.

Evaluation

Evaluation I

The fullerene derivatives according to Synthesis Examples 1 to 6 and Comparative Synthesis Examples 1 to 10 and fullerene according to Reference Example are respectively evaluated regarding a vacuum deposition through sublimation.

The evaluation is performed by increasing a temperature under high vacuum of less than or equal to a vacuum degree of 1 Pa to judge the sublimation or not, and herein, a compound having a weight loss as the temperature is increased and $T_s$(° C.) (−90 wt %) is judged to have a sublimable structure.

In Table 1, a sublimable compound is marked as "O," but a non-sublimable compound is marked as "X."

TABLE 1

|  | Ts(° C.) (−10 wt %) | Ts(° C.) (−50 wt %) | Ts(° C.) (−90 wt %) | Sublimable or not |
|---|---|---|---|---|
| Synthesis Example 1 | 330 | 390 | 450 | ○ |
| Synthesis Example 2 | 390 | 440 | 470 | ○ |
| Synthesis Example 3 | 380 | 440 | 460 | ○ |
| Synthesis Example 4 | 360 | 400 | 470 | ○ |
| Synthesis Example 5 | 350 | 390 | 460 | ○ |
| Synthesis Example 6 | 350 | 390 | 460 | ○ |
| Comparative Synthesis Example 1 | 550 | — | — | X |
| Comparative Synthesis Example 2 | 550 | — | — | X |
| Comparative Synthesis Example 3 | 330 | 390 | 450 | ○ |
| Comparative Synthesis Example 4 | 380 | 440 | 470 | ○ |
| Comparative Synthesis Example 5 | 320 | 520 | 560 | X (C60 sublimation after decomposition of substituent) |
| Comparative Synthesis Example 6 | 550 | — | — | X (polymerization) |
| Comparative Synthesis Example 7 | 320 | 520 | 560 | X (C60 sublimation after decomposition of substituent) |
| Comparative Synthesis Example 8 | 560 | — | — | X (polymerization) |
| Comparative Synthesis Example 9 | 540 | — | — | X (polymerization) |
| Comparative Synthesis Example 10 | 330 | 520 | 560 | X (C60 sublimation after decomposition of substituent) |
| Reference Example (fullerene) | 450 | 510 | 600 | ○ |

* Ts(° C.) (−10 wt %): a temperature where a sample has a 10 wt % weight loss
* Ts(° C.) (−50 wt %): a temperature where a sample has a 50 wt % weight loss
* Ts(° C.) (−90 wt %): a temperature where a sample has a 90 wt % weight loss Referring to Table 1, the fullerene derivatives according to Synthesis Examples 1 to 6 and Comparative Synthesis Examples 3 and 4 and the fullerene according to Reference Example turn out to be a compound depositable ("configured to be deposited") through ("based on") sublimation.

Evaluation II

The fullerene or fullerene derivative according to Synthesis Examples and Comparative Synthesis Example is respectively deposited on a glass substrate, and an energy level of each obtained thin film is measured. A HOMO energy level of the thin film is measured by using a photoelectron spectroscope (AC-3, RIKEN KEIKI Co. Ltd.), an optical absorption edge of the thin film is called to be an energy band gap, and a LUMO energy level is obtained by subtracting the HOMO energy level from the energy band gap.

The results are shown in Table 2.

TABLE 2

|  | HOMO (eV) | LUMO (eV) |
|---|---|---|
| Synthesis Example 1 | 6.1 | 4.0 |
| Synthesis Example 2 | 6.0 | 3.9 |
| Synthesis Example 3 | 6.1 | 4.0 |
| Synthesis Example 4 | 6.4 | 4.3 |
| Synthesis Example 5 | 6.7 | 4.7 |
| Synthesis Example 6 | 6.9 | 4.9 |
| Comparative Synthesis Example 3 | 5.7 | 3.3 |

TABLE 2-continued

|  | HOMO (eV) | LUMO (eV) |
|---|---|---|
| Comparative Synthesis Example 4 | 5.6 | 3.6 |
| Reference Example (fullerene) | 6.3 | 4.2 |

Whether or not the fullerene derivatives are appropriate for an n-type semiconductor is examined by comparing energy levels of a p-type semiconductor represented by Chemical Formula X and a p-type semiconductor represented by Chemical Formula Y based on the obtained energy levels.

[Chemical Formula X]

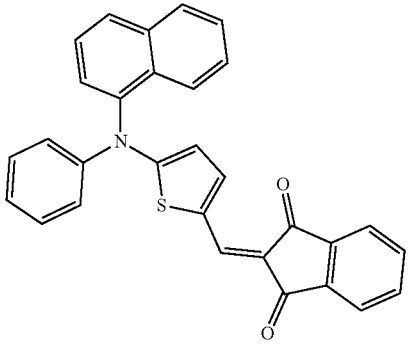

(HOMO energy level: 5.3 eV, LUMO energy level: 3.2 eV)

[Chemical Formula Y]

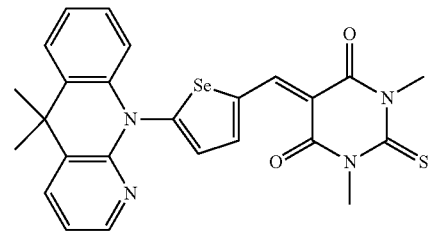

(HOMO energy level: 5.6 eV, LUMO energy level: 3.5 eV)

Accordingly, the fullerene derivatives according to Synthesis Examples 1 to 6 and the fullerene according to Reference Example have deeper HOMO and LUMO energy levels than those of the p-type semiconductor and thus may be used as an n-type semiconductor when the p-type semiconductor is used.

Evaluation III

Light absorption characteristics of each thin film formed by respectively depositing the fullerene or the fullerene derivative according to Synthesis Examples and Comparative Synthesis Examples on a glass substrate are evaluated.

The light absorption characteristics are evaluated by measuring light absorbance of a wavelength in an ultraviolet visible-near-infrared light region by using a UV-Vis spectrometer (Shimadzu Corp.).

Figure 7:
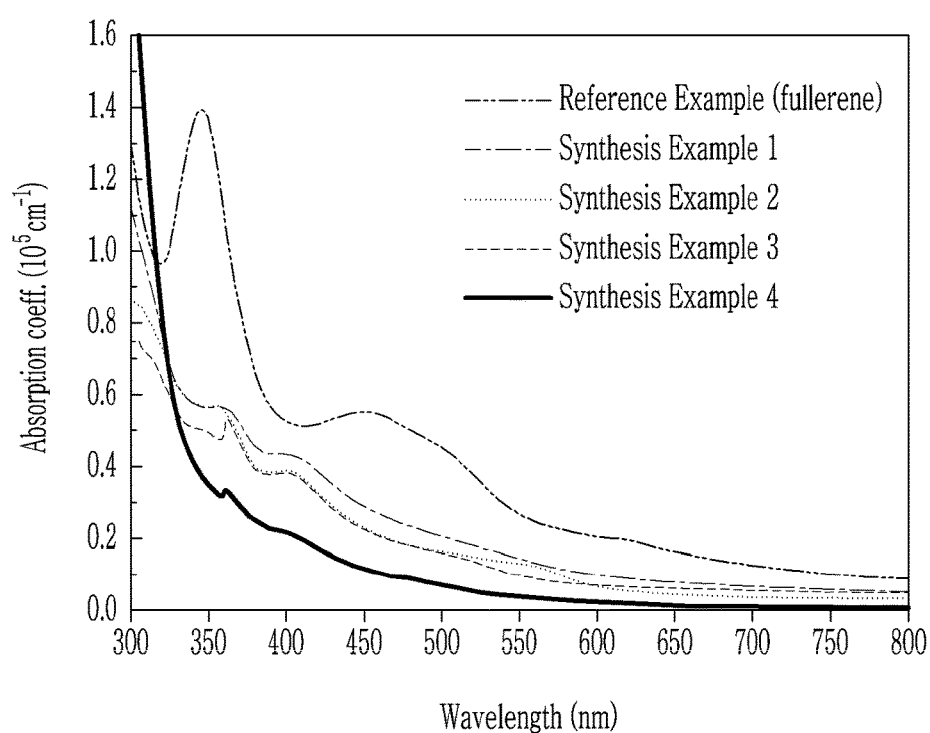
FIG. 7 is a graph showing light absorption characteristics of the fullerene or fullerene derivatives according to Synthesis Examples 1 to 4 and Reference Example.

The results are shown in Table 3 and FIG. 7.

FIG. 7 is a graph showing light absorption characteristics of the fullerene or fullerene derivatives according to Synthesis Examples 1 to 4 and Reference Example.

TABLE 3

| | Abs.coeff. 450 nm (10⁵ cm⁻¹) |
|---|---|
| Synthesis Example 1 | 0.3 |
| Synthesis Example 2 | 0.2 |
| Synthesis Example 3 | 0.2 |
| Synthesis Example 4 | 0.1 |
| Synthesis Example 5 | 0.1 |
| Synthesis Example 6 | 0.1 |
| Reference Example (fullerene) | 0.6 |

Referring Table 3 and FIG. 7, the thin films respectively including the fullerene derivatives according to Synthesis Examples 1 to 6 show low light absorption in a blue wavelength spectrum of light near to about 450 nm compared with the thin film including the fullerene according to Reference Example. Accordingly, the fullerene derivatives according to Synthesis Examples 1 to 6 show no shift of an absorption peak due to an aggregation.

Evaluation IV

A compound represented by Chemical Formula X as a p-type semiconductor (HOMO energy level: 5.3 eV, LUMO energy level: 3.2 eV) and the fullerene derivative according to Synthesis Example 1 or the fullerene according to Reference Example as an n-type semiconductor are codeposited in a volume ratio of 1:1 to form a thin film, and light absorption characteristics of the thin film are evaluated.

[Chemical Formula X]

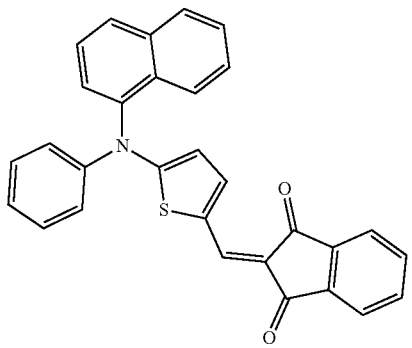

Figure 8:
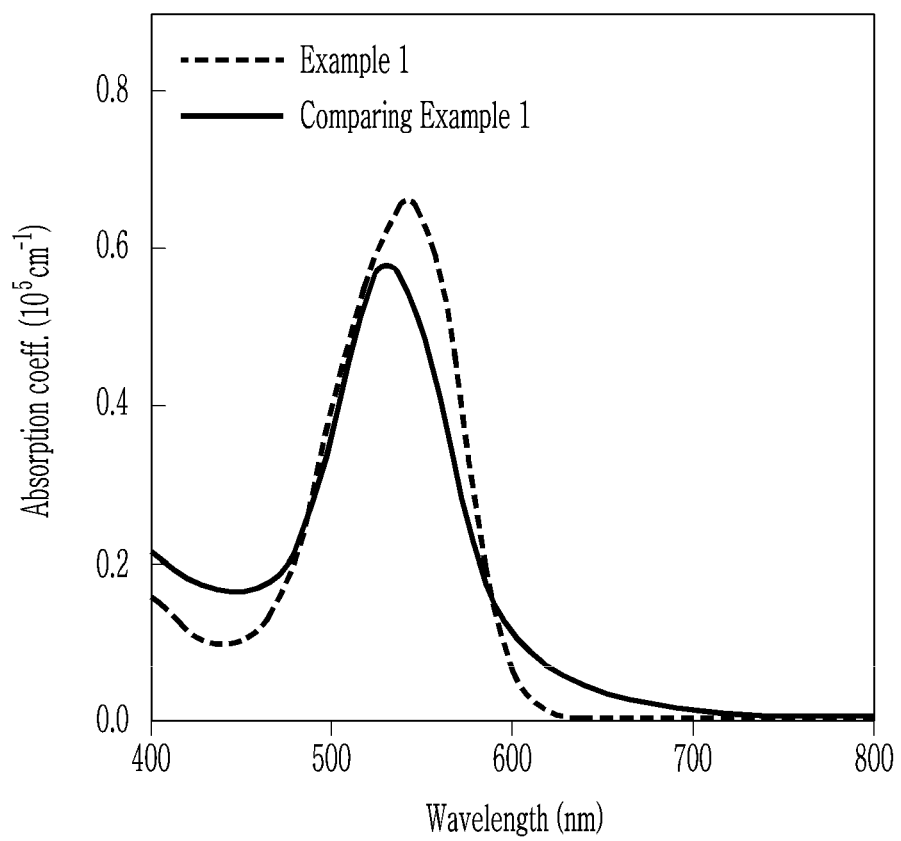
FIG. 8 is a graph showing light absorption characteristics of a film obtained by codepositing the fullerene derivative according to Synthesis Example 1 and fullerene according to Reference Example with a p-type semiconductor.

FIG. 8 is a graph showing light absorption characteristics of a film obtained by codepositing the fullerene derivative according to Synthesis Example 1 and the fullerene according to Reference Example with a p-type semiconductor.

Referring to FIG. 8, the thin film formed by codepositing the fullerene derivative according to Synthesis Example 1 and the p-type semiconductor shows low light absorption characteristics in a blue wavelength spectrum of light around 450 nm compared with the thin film formed by codepositing the fullerene according to Reference Example and the p-type semiconductor. Accordingly, the fullerene derivative according to Synthesis Example 1 shows no shift of an absorption peak according to an aggregation and may increase wavelength selectivity in a green wavelength spectrum of light when used with the p-type semiconductor.

While this disclosure has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims.

What is claimed is:

1. A compound, comprising:
a fullerene derivative represented by Chemical Formula 1:

[Chemical Formula 1]

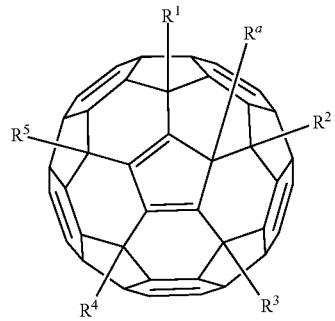

wherein, in Chemical Formula 1, $R^a$ is hydrogen or a C1 to C10 alkyl group, $R^1$ to $R^5$ are independently one of a substituted or unsubstituted C1 to C10 alkyl group, or a substituted or unsubstituted C6 to C12 aryl group, and at least one of $R^1$ to $R^5$ is a C1 to C10 alkyl group substituted with at least one of a fluorine and a cyano group, or a C6 to C12 aryl group substituted with at least one of a fluorine and a cyano group.

2. The compound of claim 1, wherein the fullerene derivative is a compound that is configured to be vacuum-deposited based on sublimation.

3. The compound of claim 2, wherein the fullerene derivative is configured to, at a pressure of 1 Pa or less, have an about 10 wt % weight loss relative to an initial weight at a temperature of less than or equal to about 450° C., have an about 50 wt % weight loss relative to an initial weight at a temperature of less than or equal to about 510° C., and have an about 90 wt % weight loss relative to an initial weight at a temperature of less than or equal to about 600° C.

4. The compound of claim 1, wherein the fullerene derivative has a LUMO energy level of about 3.7 eV to about 5.0 eV and a HOMO energy level of about 5.8 eV to about 7.0 eV.

5. The compound of claim 1, wherein $R^1$ to $R^5$ are independently one of a C1 to C10 alkyl group substituted with at least one of a fluorine and a cyano group, or a C6 to C12 aryl group substituted with at least one of a fluorine and a cyano group.

6. The compound of claim 1, wherein the fullerene derivative is represented by one of Chemical Formulae 1a to 1l:

[Chemical Formula 1a]
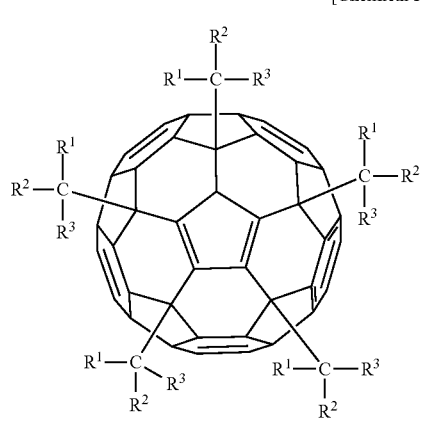
[Chemical Formula 1b]
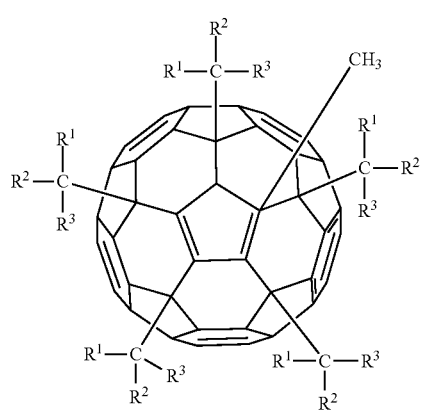
[Chemical Formula 1c]
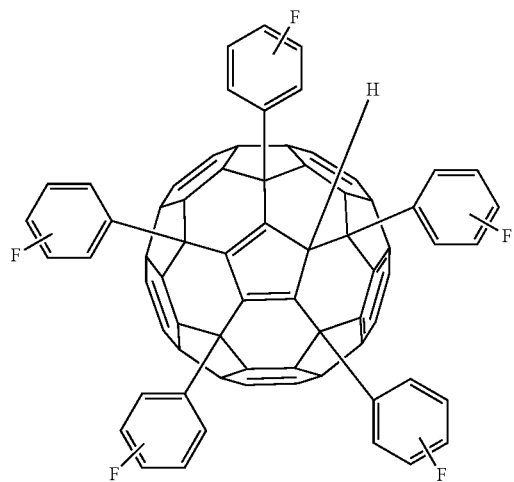
[Chemical Formula 1d]
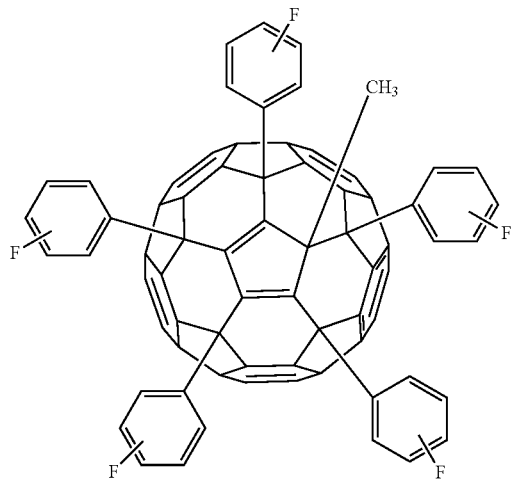
[Chemical Formula 1e]
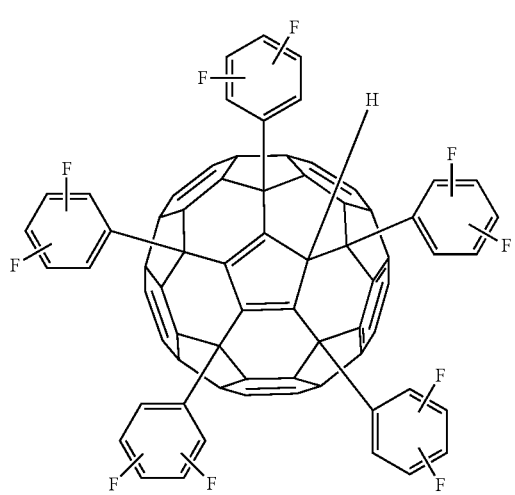
[Chemical Formula 1f]
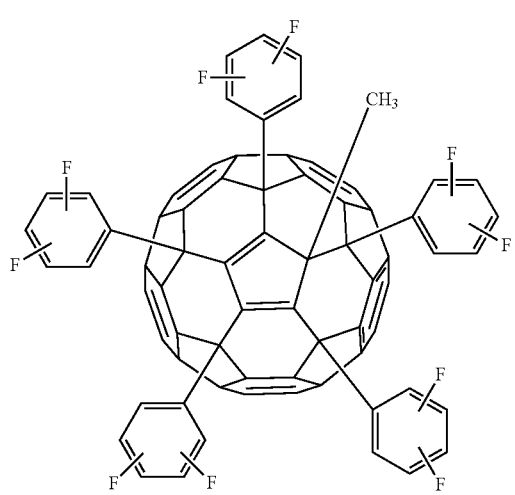

[Chemical Formula 1g]
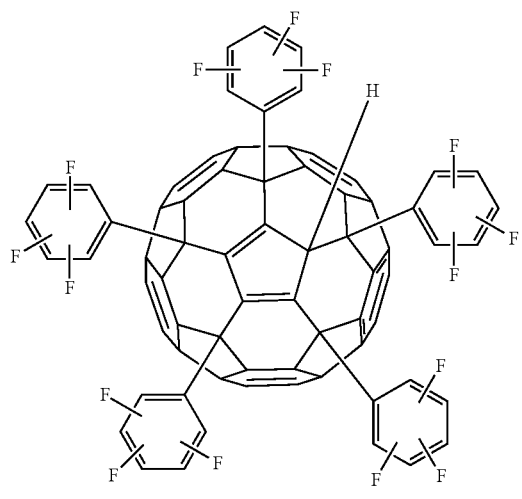
[Chemical Formula 1h]
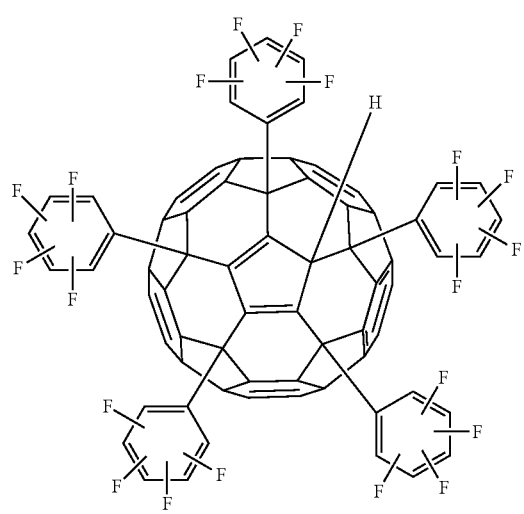
[Chemical Formula 1i]
[Chemical Formula 1j]
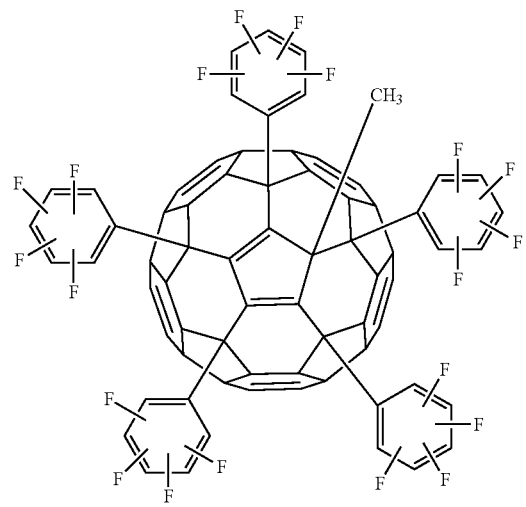
[Chemical Formula 1k]
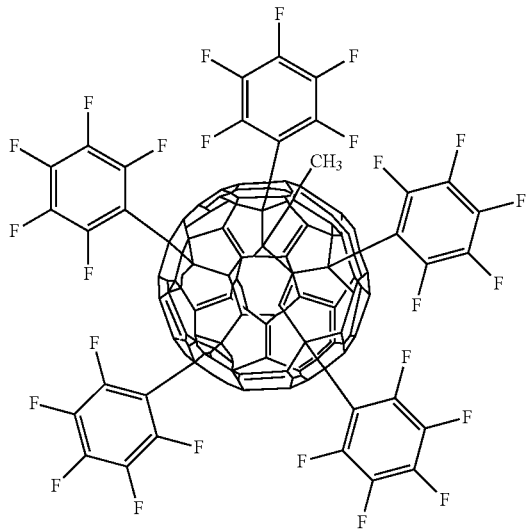
[Chemical Formula 1l]

wherein, in Chemical Formulae 1a and 1b,

R¹ to R³ are independently one of hydrogen or a fluorine and at least one of R¹ to R³ is a fluorine.

7. A thin film comprising the compound of claim 1.

8. The thin film of claim 7, wherein the thin film is associated with a peak absorption wavelength ($\lambda_{max}$) that is shorter than a peak absorption wavelength ($\lambda_{max}$) of a thin film including C60 fullerene.

9. A photoelectric device, comprising:

a first electrode and a second electrode facing each other, and an organic layer between the first electrode and the second electrode wherein the organic layer includes a fullerene derivative represented by Chemical Formula 1:

[Chemical Formula 1]

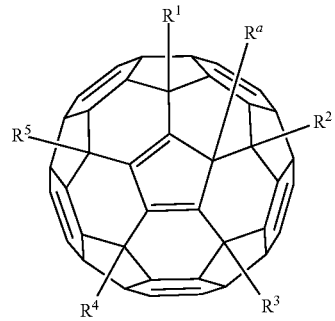

wherein, in Chemical Formula 1, $R^a$ is hydrogen or a C1 to C10 alkyl group,

R¹ to R⁵ are independently one of a substituted or unsubstituted C1 to C10 alkyl group or a substituted or unsubstituted C6 to C12 aryl group, and at least one of R¹ to R⁵ is a C1 to C10 alkyl group substituted with at least one of a fluorine and a cyano group, or a C6 to C12 aryl group substituted with at least one of a fluorine and a cyano group.

10. The photoelectric device of claim 9, wherein R¹ to R⁵ of Chemical Formula 1 are independently one of a C1 to C10 alkyl group substituted with at least one of a fluorine and a cyano group, or a C6 to C12 aryl group substituted with at least one of a fluorine and a cyano group.

11. The photoelectric device of claim 9, wherein the fullerene derivative is represented by one of Chemical Formulae 1a to 1l:

[Chemical Formula 1a]

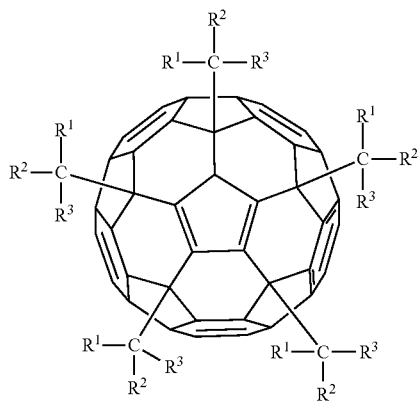

[Chemical Formula 1b]

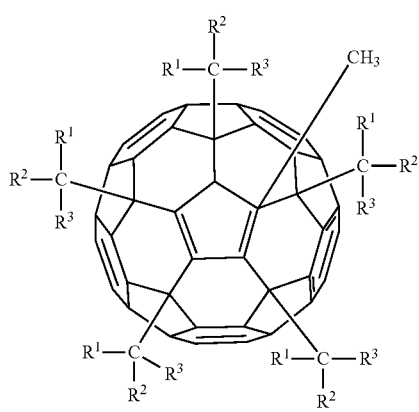

[Chemical Formula 1c]

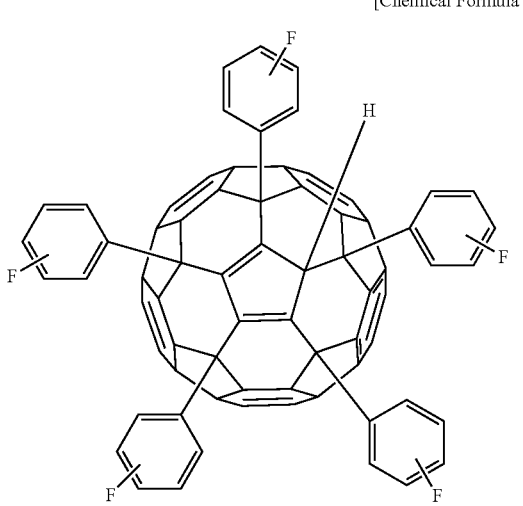

-continued
[Chemical Formula 1d]
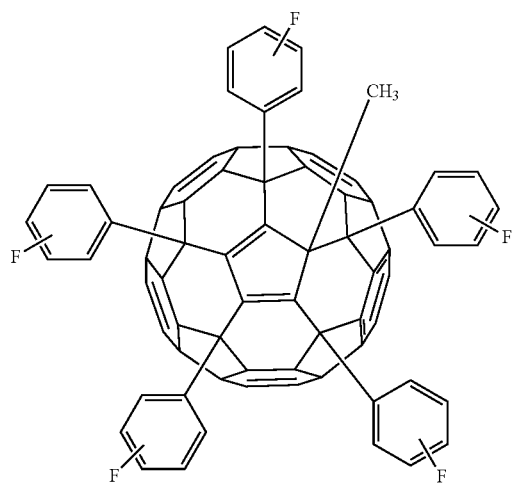
[Chemical Formula 1e]
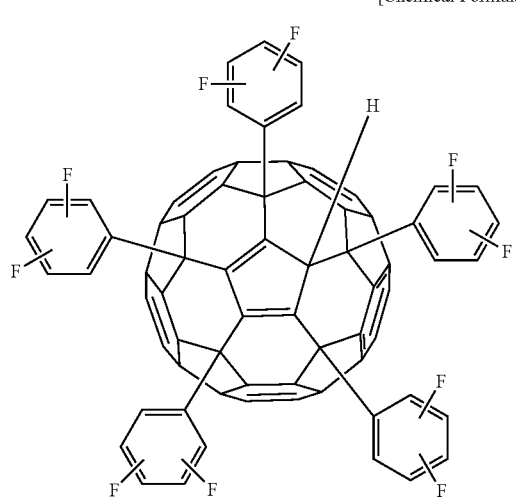
[Chemical Formula 1f]
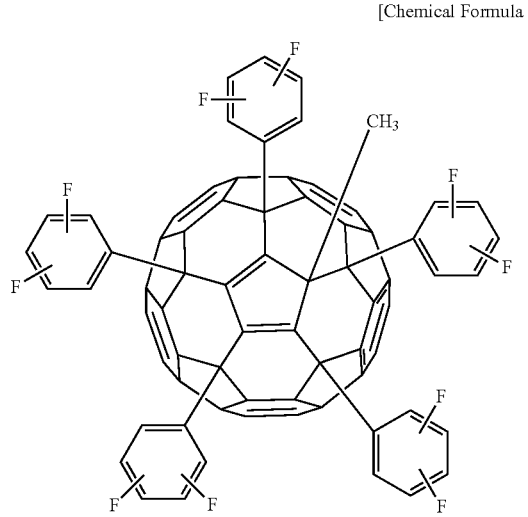
-continued
[Chemical Formula 1g]
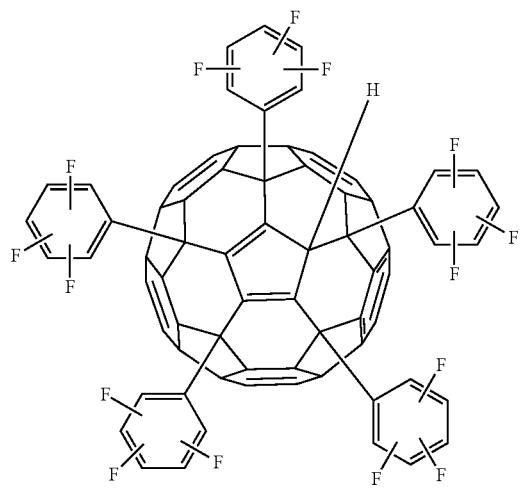
[Chemical Formula 1h]
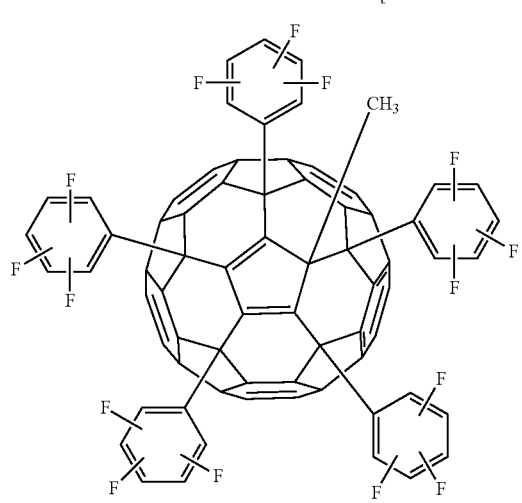
[Chemical Formula 1i]
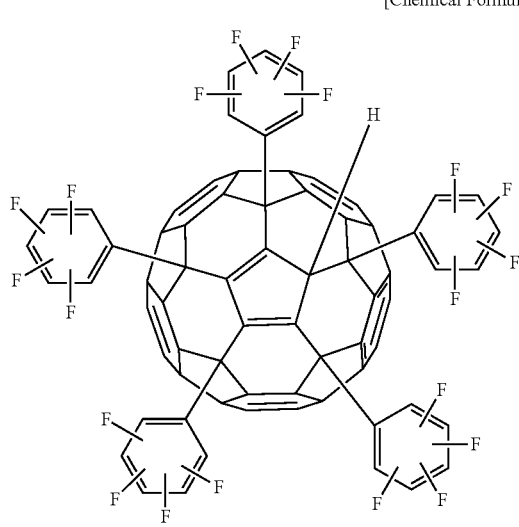

[Chemical Formula 1j]

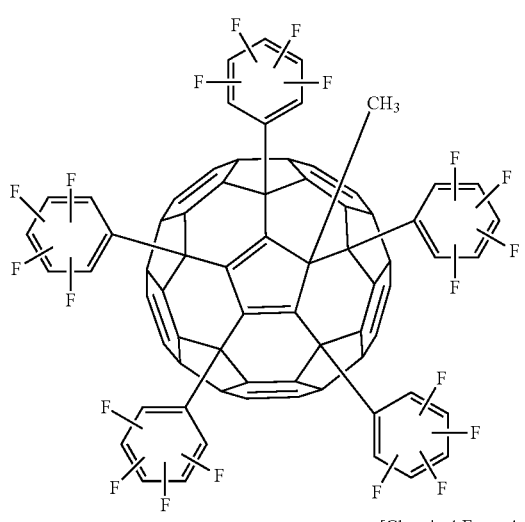

[Chemical Formula 1k]

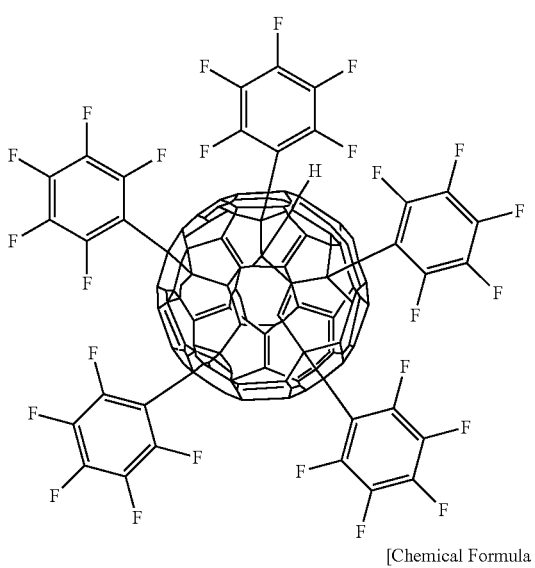

[Chemical Formula 1l]

wherein, in Chemical Formula 1a, $R^1$ to $R^3$ is hydrogen or a fluorine, and at least one of $R^1$ to $R^3$ is a fluorine.

12. The photoelectric device of claim 9, wherein the organic layer includes an active layer, the active layer includes a p-type semiconductor and an n-type semiconductor that at least partially comprise a pn junction, and the n-type semiconductor includes the fullerene derivative.

13. The photoelectric device of claim 12, wherein the p-type semiconductor and the n-type semiconductor are configured to be co-deposited based on sublimation.

14. The photoelectric device of claim 12, wherein the fullerene derivative has a LUMO energy level of about 3.7 eV to about 5.0 eV and a HOMO energy level of about 5.8 eV to about 7.0 eV.

15. The photoelectric device of claim 14, wherein the p-type semiconductor has a LUMO energy level of about 3.0 eV to about 3.6 eV and a HOMO energy level of about 5.1 eV to about 5.7 eV.

16. The photoelectric device of claim 15, wherein the p-type semiconductor is a light absorbing material having a core structure including an electron donating moiety, a pi conjugation linking group, and an electron accepting moiety.

17. The photoelectric device of claim 16, wherein the p-type semiconductor includes a compound represented by Chemical Formula 2:

[Chemical Formula 2]

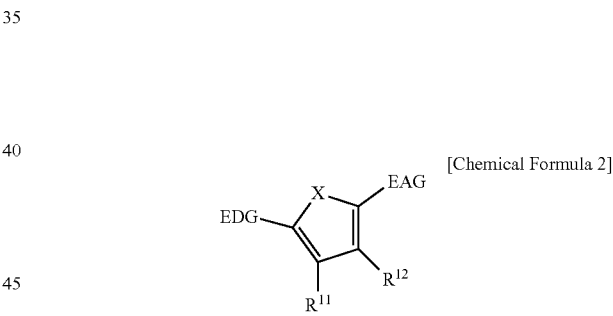

wherein, in Chemical Formula 2,

X is Se, Te, SO, $SO_2$, or $SiR^aR^b$,

EDG is an electron donating group,

EAG is an electron accepting group, and $R^{11}$, $R^{12}$, $R^a$, and $R^b$ are independently one of hydrogen or a monovalent substituent.

18. An electronic device comprising the photoelectric device of claim 9.

19. An image sensor comprising the photoelectric device of claim 9.

* * * * *